United States Patent [19]

Taylor, Jr. et al.

[11] Patent Number: 4,558,132
[45] Date of Patent: Dec. 10, 1985

[54] NITRO, AMINO AND AROYLAMINO-N-PHENYLPYRIDINAMINES IN A PROCESS FOR PREPARING PYRIDO[1,4]BENZODIAZEPINES

[75] Inventors: Chandler R. Taylor, Jr., Mechanicsville; Young S. Lo, Richmond, both of Va.

[73] Assignee: A. H. Robins Company, Incorporated, Richmond, Va.

[21] Appl. No.: 394,551

[22] Filed: Jul. 2, 1982

[51] Int. Cl.[4] .................. C07D 213/44; C07D 211/72; C07D 211/84; C07D 409/00
[52] U.S. Cl. .................................. 546/262; 546/307; 546/308; 546/284
[58] Field of Search .................. 564/73; 546/307, 308, 546/284, 262

[56] References Cited

U.S. PATENT DOCUMENTS 3,590,037  6/1971  Benko et al. ..................... 546/307

Primary Examiner—Henry R. Jiles
Assistant Examiner—Robert C. Whittenbaugh

[57] ABSTRACT

Nitro, amino and aroylamino-N-phenylpyridinamines as chemical intermediates and/or having antidepressant activity having the formula

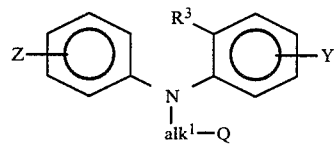

wherein $R^3$ is nitro, amino or aroylamino, and Q is hydrogen, $-NR^1R^2$ or halogen are disclosed in a process for preparing pyrido[1,4]benzodiazepines.

32 Claims, No Drawings

NITRO, AMINO AND AROYLAMINO-N-PHENYLPYRIDINAMINES IN A PROCESS FOR PREPARING PYRIDO[1,4]BENZODIAZEPINES

BACKGROUND OF THE INVENTION

1. Field of Invention

The present invention is concerned with novel nitro, amino and aroylamino-N-phenylpyridinamines, methods of preparation and use in a process for the preparation of certain pyrido[1,4]benzodiazepines which are substituted on the solitary bridging nitrogen by alkyl and aminoalkyl radicals. The pyridobenzodiazepines are antidepressants.

2. Description of the Prior Art

Wander, A. in British Pat. No. 907,646 discloses preparation of [1,4]dibenzodiazepines which are substituted on the solitary bridging nitrogen by alkyl or amino-dialkyl radicals. The route of preparation used by Wander is via nitro, amino and aroylamino-N-diphenylamines.

Japanese patent No. 73/43,520 (C.A. 80, 133501n) discloses 6-phenyl-2,3,4,4a-tetrahydro-11H-pyrido[2,3-b][1,4]benzodiazepines having anticonvulsant activity illustratively prepared from 2-aminobenzophenones and ornithine.

2-Anilino-3-nitropyridines have been prepared by Clark, R. L. et al in J. Med. Chem. (1978), Vol. 21, No. 9, pp 965–978 from an appropriate aniline and 2-chloro-3-nitropyridine. Bishop, R. R. et al. studied the kinetics of the reaction of 2-chloro-5-nitro and 2-chloro-3-nitropyridines with certain anilines as reported in J. Chem. Soc. 437 (1952).

The novel pyrido[1,4]benzodiazepines as antidepressant agents prepared via [2-[(aminopyridinyl)amino]-phenyl]aryl methanones are the subject of copending application Ser. No. 305,080, filed on Sept. 24, 1981.

SUMMARY AND OBJECTS OF THE INVENTION

The novel intermediates, the nitro, the amino and the aroylamino-N-phenylpyridinamines of this invention used in the various steps of the process for the preparation of pyrido[1,4]benzodiazepines are represented by the composite formula

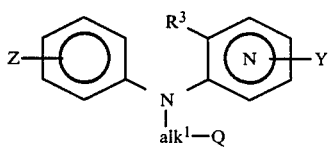

Formula I wherein;

Q is selected from the group consisting of hydrogen, —NR$^1$R$^2$ or halogen;

R$^1$ and R$^2$ are selected from the group consisting of loweralkyl or taken together with the adjacent nitrogen atom form a heterocyclic residue selected from 1-phthalimido 4-morpholinyl, 1-pyrrolidinyl, 1-piperidinyl, 4-substituted-1 piperazinyl or 1-piperazinyl;

R$^3$ is nitro, amino or aroylamino, i.e, ArC(O)NH—;

Ar is selected from the group consisting of 2 or 3-thienyl, 2, 3 or 4-pyridinyl, phenyl or phenyl substituted by 1 to 3 radicals selected from halo, loweralkyl, loweralkoxy, trifluoromethyl or nitro and may be the same or different;

Alk$^1$ is a straight or branched hydrocarbon chain containing 1–8 carbon atoms;

Z is selected from the group consisting of hydrogen, halogen, loweralkyl, loweralkoxy or nitro;

Y is selected from the group consisting of hydrogen or 1–2 radicals selected from loweralkyl or loweralkoxy and may be the same or different;

and the acid addition salts thereof.

Generally, in the process of this invention, phenylnitropyridinamines substituted on the solitary bridging nitrogen with an alkyl radical or an —alk$^1$NR$^1$,R$^2$ radical wherein R$^1$ and R$^2$ are as defined above, excluding hydrogen, are prepared, the nitro radical is reduced to amino, and this amino radical is aroylated. The resulting arylamide is cyclized to the phenyl substituted-pyrido[1,4]benzodiazepine having the formula

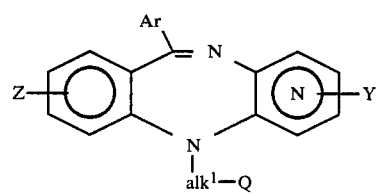

Formula X wherein Ar, Y, Z, alk$^1$ and Q have the values given under Formula I above. The compounds of Formula X are antidepressant agents except those wherein Q is 1-phthalimido, halo and certain piperazines blocked or protected in the 4-position, all of which exceptions are convertible to other antidepressant compounds of Formula X as described below.

As indicated by the foregoing Formula X, location of pyrido nitrogen is variable, illustratively as follows: in formulas Xa, Xb, Xc, and Xd all encompassed by Formula X.

The 6-aryl-11H-pyrido[2,3-b][1,4benzodiazepines encompassed by Formula X have the formula

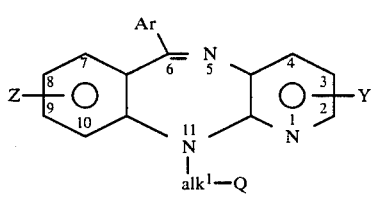

Formula Xa

The 6-aryl-11H-pyrido[3,4-b][1,4]benzodiazepines encompassed by Formula X have the formula

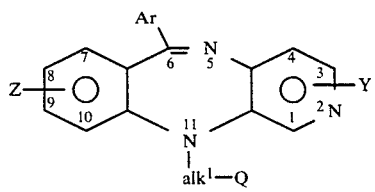

Formula Xb

The 10-aryl-5H-pyrido[4,3-b][1,4]benzodiazepines encompassed by Formula X have the formula

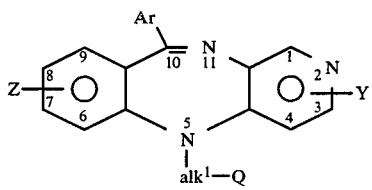

Formula Xc

The 10-aryl-5H-pyrido[3,2-b][1,4]benzodiazepines encompassed by Formula X have the formula

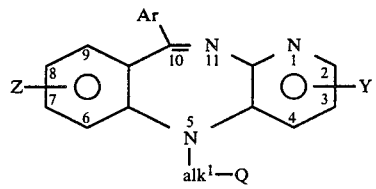

Formula Xd

As will be further recognized by the designation of indefinite position of pyrido nitrogen in Formula I, the nitro, amino and aroylamino-N-phenylpyridinamines encompassed thereby and needed to prepare the corresponding compounds of Formulas Xa, Xb, Xc, and Xd have variable position of pyrido nitrogen. The following variations Iw, Ix, Iy, and Iz encompassed by Formula I covering all positions of the pyrido nitrogen within the scope of this invention in relation to other substituents are given as follows:

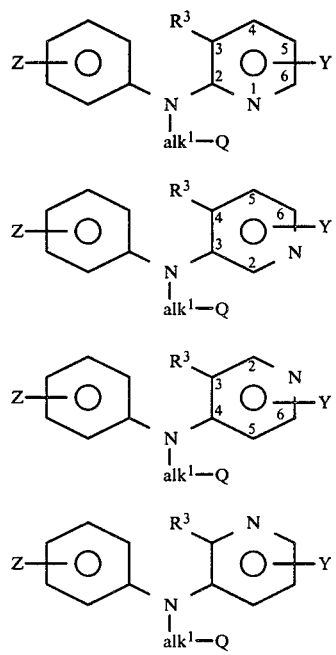

wherein $alk^1$, Y, Z, $R^3$ and Q are as defined under Formula I.

In the further definition of symbols, the term "loweralkyl", as used herein, includes straight and branched chain radicals containing 1-8 carbon atoms as, for example, methyl, ethyl, propyl, isopropyl, n-butyl, isobutyl, tertiary butyl, amyl, isoamyl, n-hexyl, n-heptyl and n-octyl radicals and the like. The "loweralkoxy" radical has the formula "—O-loweralkyl."

The "$alk^1$" straight or branched connecting hydrocarbon chain containing 1-8 carbon atoms is exemplified by methylene(—$CH_2$—), ethylene(—$CH_2$—$CH_2$—), propylene(—$CH_2CH_2CH_2$—), ethylidene[—CH—], 1,2-propylidene[—CH—$CH_2$— or
         |                              |
         $CH_3$                         $CH_3$ H                          $CH_3$
   |                           |
—$CH_2$—C—], isopropylidene[—C—] or
   |                           |
   $CH_3$                      $CH_3$ 1,3-butylene[—CH—$CH_2$—$CH_2$—]
              |
              $CH_3$ and the like.

The term halogen includes chlorine, bromine, fluorine and iodine, preferably chlorine, bromine and fluorine.

The term "4-substituted-1-piperazinyl" refers to the piperazine radical substituted in the 4-position by loweralkyl, alkoxy carbonyl or any blocking group which may subsequently be removed to give the unsubstituted piperazine radical.

By "acid addition salts" is meant salts formed with the pyrido[1,4]benzodiazepines and the nitro, amino and aroylamino-N-phenylpyridinamines which may be prepared by the process of this invention in the course of the reactions of the process or for the purpose of aiding in the isolation or purification of any compound or in any pharmaceutical preparation which utilizes a pharmaceutically acceptable acid addition salt. Examples of addition salts of strong acids are those formed with hydrochloric, sulfuric and phosphoric acids and the like. Examples of addition salts of weak acids are those formed with fumaric, maleic and oxalic acids and the like. The pharmaceutically acceptable acid addition salts are those formed with acids which are suitable for human administration.

Salts of compounds in Formula I and Formula X may be converted to the free base by partitioning between a solvent such as methylene chloride and an aqueous base such as sodium hydroxide and evaporating the solvent layer in vacuo.

For the purpose of establishing antidepressant activity of the pyrido[1,4]benzodiazepines substituted by alkyl and aminoalkyl radicals prepared via Formula I intermediates of this invention, the procedure given by Englehardt, E. L. et al. J. Med. Chem. 11 (2): 325 (1968) was followed. The compound in amount of 20 mg/kg was administered to five adult mice (ICR-DUB strain) intraperitoneally 30 min prior to the administration of a ptotic dose (32 mg/kg, I.P.) of tetrabenazine (as the methane sulfonate salt). Thirty minutes later the presence or absence of complete eyelid closure (ptosis) is assessed in each animal. An $ED_{50}$ (Median Effective Dose) may be established for any given compound in blocking tetrabenazine induced ptosis in mice following the procedure given by Litchfield, et al., J. Pharmacol. Ex. Therap. 96: 99-113 (1949).

It is therefore an object of the present invention to provide a novel and efficient process for the preparation of pyrido-[1,4]benzodiazepines substituted by alkyl and aminoalkyl radicals on the solitary bridging nitrogen.

Another object is to furnish novel nitro, amino and aroylamino-N-phenylpyridine amines which are intermediates in a process for preparing pyrido[1,4]benzodiazepines which have antidepressant activity or are useful in preparing other pyrido[1,4]benzodiazepines which have antidepressant activity.

Additional objects and advantages of the present invention will be apparent to one skilled in the art and still others will become apparent from the following description of the best mode of carrying out the present invention and the appended claims.

DETAILED DESCRIPTION OF THE INVENTION

The novel process of this invention for preparing the pyrido[1,4]benzodiazepines of foregoing Formula X comprises the steps of:

(Step 1) reacting an aniline having the formula

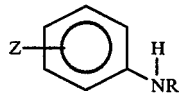
VII with a halo-nitropyridine having the formula

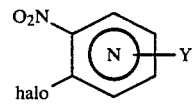
VI to produce a nitro-N-phenylpyridinamine having the formula

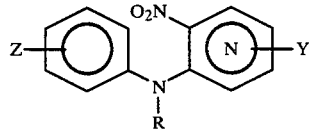
V wherein R is selected from hydrogen or loweralkyl and Y and Z are as defined above.

(Step 2) reacting a compound prepared in step 1 wherein R is hydrogen with a reagent having the formula "Q-alk$^1$-halo" wherein Q is selected from the group consisting of hydrogen, halogen or —NR$^1$R$^2$, with R$^1$ and R$^2$ being as defined above to produce a nitro-N-substituted-N-phenylpyridinamine having the formula

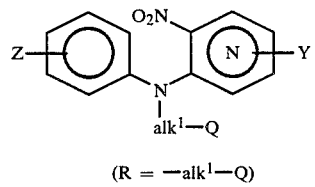
IV (R = —alk$^1$—Q)

wherein alk$^1$, Y and Z are as defined above and Q has the value corresponding to the reagent used;

(Step 3) reducing a compound prepared in step 1 wherein R is loweralkyl (Q=H) or a compound prepared in step 2 (Q may have any of above defined values including H) to give a compound having the formula

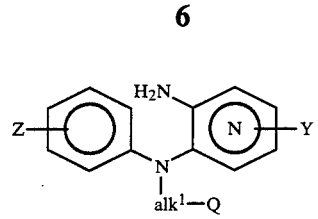
III (R = —alk$^1$—Q)

wherein alk$^1$, Y and Z are as defined above and Q has the same value as the nitro compound prior to reduction;

(Step 4) reacting the compound prepared in step 3 with an aroyl halide to produce an N-substituted-N-phenylaroylaminopyridinamine of the formula

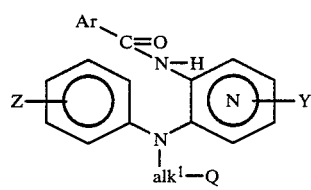
II (R = —alk$^1$Q)

wherein alk$^1$, Y, Z, Ar and Q are as defined above; and (Step 5) cyclizing a compound prepared in step 4 to the pyrido[1,4]benzodiazepine with a cyclizing agent and optionally preparing a pharmaceutically acceptable salt of the pyrido[1,4]benzodiazepine by reacting with an appropriate acid.

CHART 1

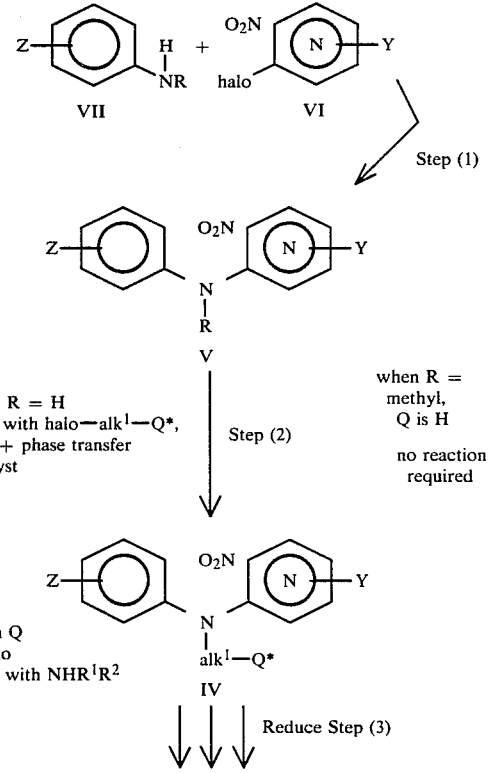

-continued
CHART 1

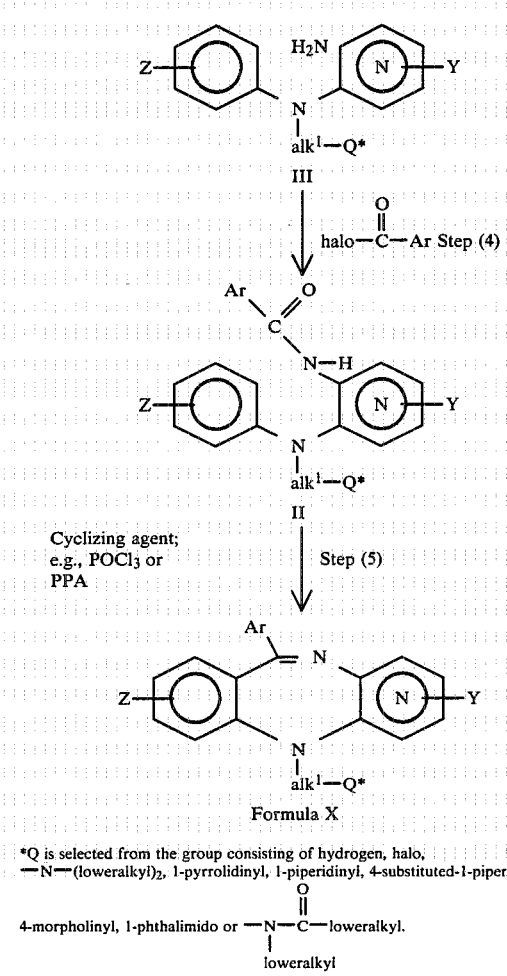

*Q is selected from the group consisting of hydrogen, halo, —N—(loweralkyl)$_2$, 1-pyrrolidinyl, 1-piperidinyl, 4-substituted-1-piperazinyl, 4-morpholinyl, 1-phthalimido or 
$$-\underset{\underset{loweralkyl}{|}}{N}-\overset{\overset{O}{\|}}{C}-loweralkyl.$$

In reference to the process of the invention as outlined above (see also Chart 1), the following further description is applicable:

In step 1, the aniline (VII) and the pyridine (VI) are usually reacted neat at about 120° C. or above until chemical ionization mass spectrometry analysis indicates formation of nitro-N-phenyl pyridinamine (V) is essentially complete. The use of a suitable carrier is not precluded, however. The unsubstituted amines (V; R=H) are suitably isolated by extraction with partitioning solvent such as chloroform and aqueous base crystallization and recrystallization from a suitable solvent. The alkyl substituted amines (V; R=loweralkyl) are conveniently isolated as hydrochloride salt by precipitation.

In step 2, the unsubstituted amines (V; R=H) are alkylaminated or radicals are introduced which will lead to "alkylamination" with an appropriate reagent represented by "halo-alk$^1$-Q" wherein Q is selected from values as defined in Chart 1, together with a base in solution with heating usually at reflux of a solvent, suitably toluene. Many agents are suitable aids in the reaction such as sodium hydride as base in an aprotic solvent such as dimethylformamide, sodium hydroxide as base in two phase reaction using water and organic solvents such as methylene chloride or toluene with no catalyst or phase transfer catalysts such as crown ether, ultrasonic wave, quaternary ammonium salts and phosphonium salts. Quaternary ammonium salts are preferred as phase transfer catalyst, preferably tetrabutyl ammonium bromide. The course of the reaction may be followed by thin-layer chromatography and/or chemical ionization mass spec analysis. The "alkylaminated" nitropyridinyl-phenylamine (IV) may be purified by washing with water, concentrating, re-dissolving in a solvent, suitably ethyl acetate, decolorizing with charcoal, filtering through a celite bed and precipitating as an acid addition salt and recrystallizing the salt from a suitable solvent. The pure free bases of Formula IV may be obtained by partitioning between a solvent and dilute base and evaporating the solvent.

In step 3, the nitro group is reduced to an amino group by any one of several methods; for example, with
(a) palladium/C+hydrogen,
(b) iron powder and acetic acid, and
(c) zinc powder and base The compounds (III) may be isolated as salts and purified by usual methods and converted to free bases by the procedures used to obtain free bases in step 2.

In step 4, aroylamino compounds, i.e., arylamides (II), are obtained by reacting with an appropriate aroyl halide in excess or an aroyl halide in an aprotic solvent; e.g. refluxing toluene or methylene chloride with or without a base at elevated temperature. Ionization mass spectrum analysis and/or NMR indicates when the reaction is complete. The crude benzamide is separated from impurities by various washing and extraction procedures finally into an organic solvent, which solution is decolorized and evaporated to dryness. The benzamides may be further purified by column chromatography and precipitation or by recrystallizing from an appropriate solvent.

In step 5, the arylamides (II) are cyclized by heating together with a cyclodehydrating agent such as phosphorus oxychloride or polyphosphoric acid to give the pyrido[1,4]benzodiazepines of Formula X which are separated from starting materials and impurities by appropriate means, usually as an acid addition salt.

Complete purification of intermediates in the various steps of the process is not always necessary, as illustrated in Example 67.

Compounds of Formula X wherein Q is 1-phthalimido may be reacted with hydrazine or acid to prepare antidepressant pyrido[1,4]benzodiazepines wherein in the Q radical —NR$^1$R$^2$, R$^1$ and R$^2$ are both hydrogen.

Compounds of Formula X wherein Q is 4-substituted-piperazine-1-yl such as t-butoxycarbonyl may be converted to antidepressant pyrido[1,4]benzodiazepines wherein the Q radical is 1-piperazine by removing the protecting group by acid hydrolysis.

Compounds of Formula X wherein Q is halo may be converted to antidepressant pyrido[1,4]benzodiazepines wherein the Q radical is —NR$^1$R$^2$ by reacting with the appropriate amine.

The preparation of the novel intermediates of Formula I and the novel process of the present invention is exemplified more fully by the following examples. Structures of intermediates are in Tables 1–3 and structures of pyrido[1,4]benzodiazepines are in Table 4. The scope of the invention is not limited thereto, however.

EXAMPLE 1

3-Nitro-N-phenyl-2-pyridinamine

A mixture of 15 g (0.10 mole) of 2-chloro-3-nitro pyridine and 9.3 g (0.10 mole) of aniline were heated by means of an oil bath at about 120° C. for 30 min. The mass spectra of a sample taken at 15 min indicated presence mainly of the title compound. The product was partitioned between chloroform and aqueous basic solution (sodium hydroxide). The aqueous solution was washed twice more with chloroform. The chloroform extracts were washed once with a sodium chloride-sodium bicarbonate solution, dried over sodium sulfate, filtered and evaporated to give 21.9 g of black oil which solidified on standing. The solid was triturated in 30–60 pet-ether for 1 hr. The remaining solid was filtered off and washed with the same solvent and air dried to give 18.7 g (87%). The solid was recrystallized from cyclohexane. Nuclear magnetic resonance confirmed the title compound, m.p. 172°–174° C.

Analysis: Calculated for $C_{19}H_9N_3O_2$: C,61.39; H,4.22; N,19.53. Found: C,61.48; H,4.19; N,19.50.

EXAMPLE 2a TO d

When in accordance with the procedure of example 1, equal molar amounts of the following are substituted for aniline,
p-methylaniline,
m-methoxyaniline,
p-chloroaniline, and
p-bromoaniline,
there are obtained:
(a) N-(4-methylphenyl)-3-nitro-2-pyridinamine,
(b) N-(3-methoxyphenyl)-3-nitro-2-pyridinamine,
(c) N-(4-chlorophenyl)-3-nitro-2-pyridinamine, and
(d) N-(4-bromophenyl)-3-nitro-2-pyridinamine.

EXAMPLE 3a TO e

When in accordance with the procedure of example 1, equal molar amounts of the following are substituted for 2-chloro-3-nitropyridine:
2-chloro-3-nitro-5-methoxypyridine,
3-chloro-4-nitropyridine,
2-methoxy-4-nitro-5-chloropyridine,
3-nitro-4-chloropyridine, and
2-nitro-3-chloropyridine,
there are obtained:
(a) 5-methoxy-3-nitro-N-phenyl-2-pyridinamine,
(b) 4-nitro-N-phenyl-3-pyridinamine
(c) 6-methoxy-4-nitro-N-phenyl-3-pyridinamine,
(d) 3-nitro-N-phenyl-4-pyridinamine,
(e) 2-nitro-N-phenyl-3-pyridinamine.

EXAMPLE 4

When in accordance with the procedure of example 1, equal molar amounts of the following are simultaneously substituted for aniline and 2-chloro-3-nitropyridine:
p-methylaniline, and
3-chloro-4-nitropyridine,
there is obtained:
N-(4-methylphenyl)-4-nitro-3-pyridinamine.

EXAMPLE 5a TO f

When in accordance with the procedure of example 1, equal molar amounts of the following are substituted for 3-nitro-2-chloropyridine:
2-chloro-3-nitro-4-methylpyridine,
2-chloro-3-nitro-5-methylpyridine,
2-chloro-3-nitro-6-methylpyridine,
2-chloro-3-nitro-5,6-dimethylpyridine,
2-chloro-3-nitro-6-methoxypyridine, and
4-chloro-3-nitro-2-methylpyridine,
there are obtained:
(a) 4-methyl-3-nitro-N-phenyl-2-pyridinamine,
(b) 5-methyl-3-nitro-N-phenyl-2-pyridinamine,
(c) 6-methyl-3-nitro-N-phenyl-2-pyridinamine,
(d) 5,6-dimethyl-3-nitro-N-phenyl-2-pyridinamine,
(e) 6-methoxy-3-nitro-N-phenyl-2-pyridinamine, and
(f) 2-methyl-3-nitro-N-phenyl-4-pyridinamine.

EXAMPLE 6

N-Methyl-3-nitro-N-phenyl-2-pyridinamine hydrochloride

To 59 g (0.55 mole) of N-methylaniline, stirred and heated at 115°–120° C. under nitrogen atmosphere was added 79 g (0.50 mole) of 2-chloro-3-nitropyridine in four portions at 15 minute intervals. The melt was maintained at 120°–125° C. for 1 hour and then poured into 700 ml of dilute aqueous hydrochloric acid. The precipitate was collected by filtration and dried. The solid was dried and recrystallized as the hydrochloride salt from ethyl acetate-ethereal hydrogen chloride to give 88.3 g (66%) yellow solid. A portion was recrystallized from ethyl acetate-ethyl alcohol to give yellow solid, m.p. 181°–182° C. after undergoing phase changes from 165°–170° C. and at 179° C.

Analysis: Calculated for $C_{12}H_{12}N_3O_2Cl$: C,54.25; H,4.55; N,15.81; Found: C,54.23; H,4.58; N,15.91.

EXAMPLE 7

N-(4-Chlorophenyl)-N-methyl-3-nitro-2-pyridinamine

To 90 g (0.63 mole) of 4-chloro-N-methylaniline heated to 115°–120° C. under nitrogen atmosphere with stirring was added 66.3 g (0.42 mole) of 2-chloro-3-nitropyridine in four portions over a period of 80 minutes. After stirring the reaction mixture for an additional 20 minutes at 115°–120° C., the temperature was increased to 135°–140° C. for an additional 20 minute period. The hot melt was poured into 700 ml of 2N hydrochloric acid solution. Red precipitate weighing 96 g was collected and dissolved in hot acetic acid and converted to the hydrochloride salt by adding ethereal hydrogen chloride. The yield of the yellow solid was 90 g (72%). A portion of the salt was recrystallized from ethyl acetate-ethyl alcohol. On drying at 80° C. in vacuo, the hydrochloride salt dissociated to the free base, the title compound, m.p. 107°–110° C.

Analysis: Calculated for $C_{12}H_{10}N_3O_2Cl$: C,54.66; H,3.82; N,15.94. Found: C,54.49; H,3.80; N,16.06.

EXAMPLE 8

N,N-Dimethyl-N'-(3-nitro-2-pyridinyl)-N'-phenyl-propanediamine, fumarate

A mixture of 6.45 g (0.030 mole) of 3-nitro-N-phenyl-2-pyridinamine, 7.2 g (0.0456 mole) of 3-dimethylaminopropyl chloride, 0.9 g (0.003 mole) of tetra-n-butyl ammonium bromide, 15 ml of toluene and 18.0 g (0.225 mole) of 50% sodium hydroxide added lastly, was heated under reflux for 2 hr. Thin layer chromatography indicated only a trace of starting pyridinamine remained. After standing overnight, chemical ionization mass spec analysis indicated the free base of the title compound [M. wt. 301 (M+1)] was present and no starting pyridinamine [M. wt 216 (M+1)] was present. The mixture was diluted with water and toluene. The toluene layer was washed four times with water, dried and concentrated. The residue was dissolved in ethyl acetate and the solution decolorized by boiling with charcoal. The solution was filtered through a celite bed. Fumaric acid (0.06 mole) was added to the filtrate. Ethyl alcohol was added and the solution chilled for a period of time and filtered. Recrystallized from ethyl acetate-ethanol, the product weighed 4.73 g (40%), m.p. 128°–130° C.

Analysis: Calculated for $C_{20}H_{24}N_4O_6$: C,57.68; H,5.81; N,13.45. Found: C,57.54; H,5.83; N,13.39.

EXAMPLE 9a TO j

When in accordance with the procedure of example 8, equal molar amounts of the following are substituted for 3-nitro-N-phenyl-2-pyridinamine:
N-(4-methylphenyl)-3-nitro-2-pyridinamine,
N-(3-methoxyphenyl)-3-nitro-2-pyridinamine,
5-methoxy-3-nitro-N-phenyl-2-pyridinamine,
4-nitro-N-phenyl-3-pyridinamine,
N-(4-methylphenyl)-4-nitro-3-pyridinamine,
6-methoxy-4-nitro-N-phenyl-3-pyridinamine,
3-nitro-N-phenyl-4-pyridinamine,
2-nitro-N-phenyl-3-pyridinamine,
N-(4-chlorophenyl)-3-nitro-2-pyridinamine, and
N-(4-bromophenyl)-3-nitro-2-pyridinamine,
there are obtained fumarate salts of the following:
- (a) N,N-dimethyl-N'-(4-methylphenyl)-N'-(3-nitro-2-pyridinyl)propanediamine,
- (b) N-(3-methoxyphenyl)-N',N'-dimethyl-N-(3-nitro-2-pyridinyl)propanediamine,
- (c) N-(5-methoxy-3-nitro-2-pyridinyl)-N',N'-dimethyl-N-phenylpropanediamine,
- (d) N,N-dimethyl-N'-(4-nitro-3-pyridinyl)-N'-phenyl-propanediamine,
- (e) N,N-dimethyl-N'-(4-methylphenyl)-N'-(4-nitro-3-pyridinyl)propanediamine,
- (f) N-(6-methoxy-4-nitro-3-pyridinyl)-N',N'-dimethyl-N-phenylpropanediamine,
- (g) N,N-dimethyl-N'-(3-nitro-4-pyridinyl)-N'-phenyl-propanediamine,
- (h) N,N-dimethyl-N'-(2-nitro-3-pyridinyl)-N'-phenyl-propanediamine,
- (i) N,N-dimethyl-N'-(4-chlorophenyl)-N'-(3-nitro-2-pyridinyl)propanediamine, and
- (j) N,N-dimethyl-N'-(4-bromophenyl)-N'-(3-nitro-2-pyridinyl)propanediamine.

EXAMPLE 10

2-[3-[(3-Nitro-2-pyridinyl)(phenyl)amino]propyl]-1H-isoindole-1,3(2H)-dione

3-Nitro-N-phenyl-2-pyridinamine and 1-chloro-3-(1-phthalimido)propane are reacted to give the title compound.

EXAMPLE 11

N-(3-Chloropropyl)-3-nitro-N-phenyl-2-pyridinamine

When in accordance with the procedure of example 8, an equal molar amount of 1,3-dichloropropane is substituted for 3-dimethylaminopropyl chloride, the title compound is obtained.

EXAMPLE 12

3-Nitro-N-phenyl-N-(N',N'-dimethylaminopropyl)-2-pyridinamine

The title compound is prepared by reacting N-(3-chloropropyl)-3-nitro-N-phenyl-2-pyridinamine with dimethylamine.

EXAMPLE 13a AND b

When in the procedure of example 8, equal molar amounts of the following are substituted for 3-dimethylaminopropyl chloride:
2-dimethylaminoethyl chloride, and
4-dimethylaminobutyl chloride,
there are obtained:
- (a) N,N-dimethyl-N'-(phenyl)-N'-(3-nitro-2-pyridinyl)ethanediamine, and
- (b) N,N-dimethyl-N'-(phenyl)-N'-(3-nitro-2-pyridinyl)butanediamine.

EXAMPLE 14a TO d

When in the procedure of example 8, equal molar amounts of the following are substituted for 3-dimethylaminopropyl chloride:
4-(3-chloropropyl)morpholine hydrochloride,
N-(3-chloropropyl)piperidine hydrochloride,
N-(3-chloropropyl)pyrrolidine hydrochloride, and
1-(3-chloropropyl)-4-methylpiperazine dihydrochloride,
there are obtained:
- (a) 3-nitro-N-phenyl-N-(4-morpholinopropyl)-2-pyridinamine,
- (b) 3-nitro-N-phenyl-N-(1-piperidinopropyl)-2-pyridinamine,
- (c) 3-nitro-N-phenyl-N-(1-pyrrolidinopropyl)-2-pyridinamine,
- (d) 3-nitro-N-phenyl-N-(4-methylpiperazin-1-ylpropyl)-2-pyridinamine.

EXAMPLE 15a TO f

When in accordance with the procedure of example 8, equal molar amounts of the following are substituted for 3-nitro-N-phenyl-2-pyridinamine,
4-methyl-3-nitro-N-phenyl-2-pyridinamine,
5-methyl-3-nitro-N-phenyl-2-pyridinamine,
6-methyl-3-nitro-N-phenyl-2-pyridinamine,
5,6-dimethyl-3-nitro-N-phenyl-2-pyridinamine,
6-methoxy-3-nitro-N-phenyl-2-pyridinamine,
2-methyl-3-nitro-N-phenyl-4-pyridinamine,
there are obtained:
- (a) N-phenyl-N',N'-dimethyl-N-(4-methyl-3-nitro-2-pyridinyl)propanediamine,
- (b) N-phenyl-N',N'-dimethyl-N-(5-methyl-3-nitro-2-pyridinyl)propanediamine,
- (c) N-phenyl-N',N'-dimethyl-N-(6-methyl-3-nitro-2-pyridinyl)propanediamine,
- (d) N-phenyl-N',N'-dimethyl-N-(5,6-dimethyl-3-nitro-2-pyridinyl)propanediamine,
- (e) N-phenyl-N',N'-dimethyl-N-(6-methoxy-3-nitro-2-pyridinyl)propanediamine, and
- (f) N-phenyl-N',N'-dimethyl-N-(2-methyl-3-nitro-4-pyridinyl)propanediamine.

EXAMPLE 16

$N^2$-[3-(Dimethylamino)propyl]-$N^2$-phenyl-2,3-pyridinediamine

To a solution of 3.6 g of N,N-dimethyl-N'-(3-nitro-2-pyridinyl)-N'-phenylpropanediamine, obtained in Example 8, in acetic acid at 80°–100° C. was added 7 g of iron powder, portionwise, over a 5 minute period. The reaction appeared to be exothermic and the heat source was removed temporarily. Chemical ionization mass spectra indicated the reaction was complete after about 50 min. After an additional 20 min. heating time, the mixture was cooled, filtered with difficulty, washing the filter cake with methylene chloride. After dilution of the filtrate with water the layers were separated and the water layer was washed with methylene chloride. The methylene chloride layers were combined, dried and evaporated to yield 1.25 g (46.4%) product oil.

EXAMPLE 17

$N^2$-[3-(Dimethylamino)propyl]-$N^2$-phenyl-2,3-pyridinediamine dihydrochloride A solution of 16 g (0.053 mole) of N,N-dimethyl-N'-(3-nitro-2-pyridinyl)-N'-phenylpropanediamine (fumarate salt converted to free base by partitioning between aqueous base and methylene chloride and evaporating) in 150 ml of 95% ethyl alcohol was shaken in a Parr hydrogenation bottle together with 1.5 g of Palladium on Carbon (5%) under 40 psi. hydrogen pressure at room temperature. The reaction mixture was filtered through celite and the filtrate concentrated in vacuo. A portion of the residue was converted to the hydrochloride salt with ethereal hydrogen chloride which was crystallized from ethyl alcohol:ethyl acetate and recrystallized from isopropyl ether:isopropyl alcohol to give a yellow solid, m.p. 190°–192° C. (decomp.).

Analysis: Calculated for $C_{16}H_{24}N_4Cl_2$: C,55.98; H,7.05; N,16.32. Found: C,55.75; H,7.09; N,16.12.

EXAMPLE 18

When in accordance with the procedure of example 17, equal molar amounts of the following are substituted for N,N-dimethyl-N'-(3-nitro-2-pyridinyl)-N'-phenylpropanediamine:

N,N-dimethyl-N'-(4-methylphenyl)-N'-(3-nitro-2-pyridinyl)propanediamine,

N-(3-methoxyphenyl)-N',N'-dimethyl-N-(3-nitro-2-pyridinyl)propanediamine,

N-(5-methoxy-3-nitro-2-pyridinyl)-N',N'-dimethyl-N-phenylpropanediamine,

N,N-dimethyl-N'-(phenyl)-N'-(3-nitro-2-pyridinyl)ethanediamine,

N,N-dimethyl-N'-(phenyl)-N'-(3-nitro-2-pyridinyl)butanediamine,

N,N-dimethyl-N'-(4-nitro-3-pyridinyl)-N'-phenylpropanediamine,

N,N-dimethyl-N'-(4-methylphenyl)-N'-(4-nitro-3-pyridinyl)propanediamine,

N-(2-methoxy-4-nitro-5-pyridinyl)-N',N'-dimethyl-N-phenylpropanediamine,

N,N-dimethyl-N'-(3-nitro-4-pyridinyl)-N-phenylpropanediamine,

N,N-dimethyl-N'-(2-nitro-3-pyridinyl)-N'-phenylpropanediamine,

N,N-dimethyl-N'-(4-chlorophenyl)-N'-(3-nitro-2-pyridinyl)propanediamine, and

N,N-dimethyl-N'-(4-bromophenyl)-N'-(3-nitro-2-pyridinyl)propanediamine, there was obtained:
- (a) $N^2$-[3-(dimethylamino)propyl]-$N^2$-(4-methylphenyl)-2,3-pyridinediamine,
- (b) $N^2$-[3-(dimethylamino)propyl]-$N^2$-(3-methoxyphenyl)-2,3-pyridinediamine,
- (c) $N^2$-[3-(dimethylamino)propyl]-5-methoxy-$N^2$-phenyl-2,3-pyridinediamine,
- (d) $N^2$-[2-(dimethylamino)ethyl]-$N^2$-phenyl-2,3-pyridinediamine,
- (e) $N^2$-[4-(dimethylamino)butyl]-$N^2$-phenyl-2,3-pyridinediamine,
- (f) $N^3$-[3-(dimethylamino)propyl]-$N^3$-phenyl-3,4-pyridinediamine,
- (g) $N^3$-[3-(dimethylamino)propyl]-$N^3$-(4-methylphenyl)-3,4-pyridinediamine,
- (h) $N^3$-[3-(dimethylamino)propyl]-6-methoxy-$N^3$-phenyl-3,4-pyridinediamine,
- (i) $N^4$-[3-(dimethylamino)propyl]-$N^4$-phenyl-3,4-pyridinediamine,
- (j) $N^3$-[3-(dimethylamino)propyl]-$N^3$-phenyl-2,3-pyridinediamine,
- (k) $N^2$-(4-chlorophenyl)-$N^2$-[3-(dimethylamino)propyl]-2,3-pyridinediamine, and
- (l) $N^2$-(4-bromophenyl)-$N^2$-[3-(dimethylamino)propyl]-2,3-pyridinediamine.

EXAMPLE 19

2-[3-[(3-Amino-2-pyridinyl)phenylamino]propyl]-1H-isoindole-1,3(2H)dione

2-[3-[(3-Nitro-2-pyridinyl)phenylamino]propyl]-1H-isoindole-1,3(2H)dione is reduced with hydrogen and palladium-on-carbon catalyst in ethanol-ethyl acetate mixtures to give the title compound.

EXAMPLE 20

$N^2$-Methyl-$N^2$-phenyl-2,3-pyridinediamine, monohydrochloride

A mixture of 6.0 g (0.023 mole) of 2-[N-methyl-N-phenyl]-3-nitropyridinamine hydrochloride, 1.84 g (0.046 mole) of sodium hydroxide pellets, 6.0 g (0.092 mole) of zinc dust in 50 ml of 75% ethanol-$H_2O$ was heated at reflux for 1.5 hr. The reaction mixture was filtered through celite and the filtrate boiled with charcoal for 20 minutes. The charcoal was removed by filtration and the filtrate concentrated in vacuo. The hydrochloride salt was prepared by reacting the residue with ethereal hydrogen chloride and thereafter twice crystallized as the hydrochloride salt from ethyl alcohol-ethyl acetate to give 2.5 g (46%) solid, m.p. 194°–196° C.

Analysis: Calculated for $C_{12}H_{14}N_3Cl$: C,61.15; H,5.99; N,17.83. Found: C,60.96; H,6.05; N,17.83.

EXAMPLE 21

$N^2$-(4-Chlorophenyl)-$N^2$-methyl-2,3-pyridinediamine

To a stirred mixture of 50 ml of 1:1 acetic acid:water and the free base—N-(4-chlorophenyl)-N-methyl-3-nitro-pyridinamine resulting from partitioning 5.0 g of the hydrochloride salt between methylene chloride and aqueous sodium hydroxide and evaporating the methylene chloride layer was added in one portion, 120 ml of titanium chloride solution (labeled 16% but obviously had deteriorated to an unknown extent). After the reaction mixture had stirred for 30 min at room temperature, ethyl alcohol was added until solution was effected. More titanium trichloride was added in 20 ml portions until a purple color persisted (normal end point). Dilute sodium hydroxide solution was added in an amount sufficient to basify the solution. The resulting mixture was filtered through celite, washing the filter cake with methylene chloride. The aqueous portion of the filtrate was extracted with methylene chloride. All methylene chloride portions were combined, dried and concentrated in vacuo. The crystalline residue (3 g) was twice recrystallized, boiling with charcoal, from benzene-cyclohexane to give 2 g (50%) of beige colored solid, m.p. 101°–102.5° C.

Analysis: Calculated for $C_{12}H_{12}N_3Cl$: C,61.67; H,5.18; N,17.98. Found: C,61.74; H,5.13; N,17.94.

EXAMPLE 22

When in accordance with the procedure of example 17, equal molar amounts of the following are substituted for N,N-dimethyl-N'-(3-nitro-2-pyridinyl)-N¹-phenyl-propanediamine,
3-nitro-N-phenyl-N-[3-(4-morpholinyl)propyl]-2-pyridinamine,
3-nitro-N-phenyl-N-[3-(1-piperidinyl)propyl]-2-pyridinamine,
3-nitro-N-phenyl-N-[3-(1-pyrrolidinyl)propyl]-2-pyridinamine, and
3-nitro-N-phenyl-N-[3-(4-methyl-1-piperazinyl)propyl]-2-pyridinamine,
there are obtained:
(a) $N^2$-(4-morpholinyl)propyl-$N^2$-phenyl-2,3-pyridinediamine,
(b) $N^2$-phenyl-$N^2$-(1-piperidinyl)propyl-2,3-pyridinediamine,
(c) $N^2$-phenyl-$N^2$-(1-pyrrolidinyl)propyl-2,3-pyridinediamine, and
(d) $N^2$-[(4-methyl-1-piperazinyl)propyl]-$N^2$-phenyl-2,3-pyridinediamine

EXAMPLE 23

When in accordance with the procedures of example 17, equal molar amounts of the following are substituted for N,N-dimethyl-N'-(3-nitro-2-pyridinyl)-N'-phenyl-propanediamine,
N-phenyl-N',N'-dimethyl-N-(4-methyl-3-nitro-2-pyridinyl)propanediamine,
N-phenyl-N',N'-dimethyl-N-(5-methyl-3-nitro-2-pyridinyl)propanediamine,
N-phenyl-N',N'-dimethyl-N-(6-methyl-3-nitro-2-pyridinyl)propanediamine,
N-phenyl-N',N'-dimethyl-N-(5,6-dimethyl-3-nitro-2-pyridinyl)propanediamine,
N-phenyl-N',N'-dimethyl-N-(6-methoxy-3-nitro-2-pyridinyl)propanediamine, and
N-phenyl-N',N'-dimethyl-N-(2-methyl-3-nitro-4-pyridinyl)propanediamine,
there are obtained,
(a) N-(3-amino-4-methyl-2-pyridinyl)-N',N'-dimethyl-N-phenylpropanediamine,
(b) N-(3-amino-5-methyl-2-pyridinyl)-N',N'-dimethyl-N-phenylpropanediamine,
(c) N-(3-amino-6-methyl-2-pyridinyl)-N',N'-dimethyl-N-phenylpropanediamine,
(d) N-(3-amino-5,6-dimethyl-2-pyridinyl)-N',N'-dimethyl-N-phenylpropanediamine,
(e) N-(3-amino-6-methoxy-2-pyridinyl)-N',N'-dimethyl-N-phenylpropanediamine, and
(f) N-(3-amino-2-methyl-4-pyridinyl)-N',N'-dimethyl-N-phenylpropanediamine.

EXAMPLE 24

N-[2-[[3-(Dimethylamino)propyl]phenylamino]-3-pyridinyl]benzamide fumarate[1:1.5]

To a stirred solution of 3.0 g (0.011 mole) of $N^2$-[3-(dimethylamino)propyl]-$N^2$-phenyl-2,3-pyridinediamine and 1.8 g (0.018 mole) of triethylamine in 50 ml of dry methylene chloride under nitrogen atmosphere was added dropwise at 15°–20° C., 2.4 g (0.017 mole) of benzoyl chloride. The mixture was stirred for about 3 hours at room temperature after which time thin-layer chromatography indicated the starting pyridinediamine had completely reacted. The reaction mixture was filtered and the filtrate washed in sequence once with water, twice with aqueous sodium hydroxide (pH 14) and again with water followed by aqueous sodium chloride. The methylene chloride layer was dried over magnesium sulfate and concentrated on a rotary evaporator. The residue, primarily the free base of the title compound, was reacted with fumaric acid in ethyl acetate-ethyl alcohol to give the fumarate which was recrystallized from ethyl acetate-ethyl alcohol to give 1.4 g of beige colored solid, m.p. 131°–132.5° C.

Analysis: Calculated for $C_{29}H_{32}N_4O_7$: C,63.49; H,5.88; N,10.21. Found: C,63.36; H,5.87; N,10.17.

EXAMPLE 25

N-[2-[[3-(Dimethylamino)propyl]phenylamino]-3-pyridinyl]benzamide

A mixture of 10.8 g (0.05 mole) of 3-nitro-N-phenyl-2-pyridinamine, 11.9 g (0.075 mole) of 3-dimethylaminopropyl chloride, 32 g (0.4 mole) of 50% aqueous sodium hydroxide, 1 g of tetra-n-butyl ammonium bromide all in 22 ml of toluene were heated at reflux for 4 hr. The mixture was diluted with toluene and water and worked up as in Example 8, to give crude N,N-dimethyl-N'-(3-nitro-2-pyridinyl)-N'-phenyl-propanediamine as an oil. The black oil was mixed with 13 g (0.20 mole) of zinc powder, 2 g of sodium hydroxide pellets, 75 ml of 200 proof ethanol and 25 ml of water and refluxed for 1 hr. The mixture was filtered, washing with toluene and solvent evaporated. The residue was dissolved in methylene chloride, dried over magnesium sulfate and treated with charcoal. To the filtrate (ca 100 ml vol.) was added 10.6 g (0.075 mole) of benzoyl chloride and the reaction mixture refluxed gently until mass spectrum indicated reaction was complete. A small amount of methanol (2–3 ml) was added and the mixture extracted (washed) twice with sodium bicarbonate solution, back extracting the aqueous wash once with methylene chloride. Toluene was added and the mixture evaporated to an oil determined to be crude N-[2-[[3-(dimethylamino)propyl]phenylamino]-3-pyridinyl]benzamide. The oil was redissolved in 50 ml of toluene. To this solution was added 50 ml of isopropyl alcohol containing 7.5 g hydrogen chloride. Charcoal and celite filter aid was added and the mixture stirred overnight after which it was filtered, washing the cake with isopropyl alcohol, and evaporated to give a black oil. The oil was partitioned using methylene chloride and aqueous 2N hydrochloric acid solution. The methylene chloride layer was extracted once with the 2N hydrochloric acid and the aqueous layers were extracted once with toluene. The combined aqueous layers were covered with toluene and basified with 50% sodium hydroxide. The aqueous layer was extracted twice with toluene. The toluene solutions were washed with sodium bicarbonate solution and evaporated partially to give an azetropically dried solution. A solution of 7.5 g hydrogen chloride in 50 ml of isopropyl alcohol was added and the mixture treated with charcoal. The mixture was filtered, washing with isopropyl alcohol and the filtrate evaporated to give a black oil. The oil was stirred in 100 ml acetone—10 ml isopropyl alcohol mixture for about 60 hr, during which time a solid suspension formed. Ethyl acetate (200 ml) was added with stirring continued for 1 hr. The solid was separated by filtration, washing with ethyl acetate and dried under nitrogen to give 11 g yellow powder identified by mass spectra and thin layer chromatography as the title compound. Overall yield based on starting 3-nitro-N-phenyl-2-pyridinamine was 54% of theory.

EXAMPLE 26a TO 1

When in accordance with the procedure of example 24, equal molar amounts of the following are substituted for $N^2$-[3-(dimethylamino)propyl]-$N^2$-phenyl-2,3-pyridinediamine:

$N^2$-[3-(dimethylamino)propyl]-$N^2$-(4-methylphenyl)-2,3-pyridinediamine, $N^2$-[3-(dimethylamino)propyl]-$N^2$-(3-methoxyphenyl)-2,3-pyridinediamine, $N^2$-[3-(dimethylamino)propyl]-5-methoxy-$N^2$-phenyl-2,3-pyridinediamine, $N^2$-[2-(dimethylamino)ethyl]-$N^2$-phenyl-2,3-pyridinediamine, $N^2$-[4-(dimethylamino)butyl]-$N^2$-phenyl-2,3-pyridinediamine, $N^3$-[3-(dimethylamino)propyl]-$N^3$-phenyl-3,4-pyridinediamine, $N^3$-[3-(dimethylamino)propyl]-$N^3$-(4-methylphenyl)-3,4-pyridinediamine, $N^3$-[3-(dimethylamino)propyl]-6-methoxy-$N^3$-phenyl-3,4-pyridinediamine, $N^4$-[3-(dimethylamino)propyl]-$N^4$-phenyl-3,4-pyridinediamine $N^3$-[3-(dimethylamino)propyl]-$N^3$-phenyl-2,3-pyridinediamine.

$N^2$-(4-chlorophenyl)-$N^2$-[3-(dimethylamino)propyl]-2,3-pyridinediamine, and $N^2$-(4-bromophenyl)-$N^2$-[3-(dimethylamino)propyl]-2,3-pyridinediamine, there are obtained:

(a) N-[2-[[3-(dimethylamino)propyl](4-methylphenyl)amino]-3-pyridinyl]benzamide, (b) N-[2-[[3-(dimethylamino)propyl](3-methoxyphenyl)amino]-3-pyridinyl]benzamide, (c) N-[2-[[3-dimethylamino)propyl]phenylamino]-5-methoxy-3-pyridinyl]benzamide, (d) N-[2-[[3-(dimethylamino)ethyl]phenylamino]-3-pyridinyl]benzamide, (e) N-[2-[[3-(dimethylamino)butyl]phenylamino]-3-pyridinyl]benzamide, (f) N-[3-[[3-(dimethylamino)propyl]phenylamino]-4-pyridinyl]benzamide, (g) N-[3-[[3-(dimethylamino)propyl](4-methylphenyl)amino]-4-pyridinyl]benzamide, (h) N-[5-[[3-(dimethylamino)propyl]phenylamino]-6-methoxy-4-pyridinyl]benzamide, (i) N-[4-[[3-(dimethylamino)propyl]phenylamino]-3-pyridinyl]benzamide, (j) N-[3-[[3-(dimethylamino)propyl]phenylamino]-2-pyridinyl]benzamide, (k) N-[3-[(4-chlorophenyl)-[3-(dimethylamino)propyl]amino]-2-pyridinyl]benzamide, and (l) N-[3-[(4-bromophenyl)-[3-(dimethylamino)propyl]amino]-2-pyridinyl]benzamide.

EXAMPLE 27

1,3-Dihydro-N-[2-[[3-(1,3-dioxo-2H-isoindol-2-yl)propyl]phenylamino]-3-pyridinyl]benzamide 2-[3-[(3-Amino-2-pyridinyl)phenylamino]propyl]-1H-isoindole-1,3-(2H)-dione is reacted with benzoyl chloride to prepare the title compound.

EXAMPLE 28

N-[2-[[3-(Dimethylamino)propyl]phenylamino]-3-pyridinyl]-2-fluorobenzamide and oxalate[1:1]salt To a stirred solution of 9.0 g (0.033 mole) of $N^2$-[3-(dimethylamino)propyl]-$N^2$-phenyl-2,3-pyridinediamine and 4.0 g (0.040 mole) of triethylamine in 100 ml of dry methylene chloride was added dropwise at 15°-20° C., 6.1 g (0.038 mole) of 2-fluorobenzoyl chloride. The reaction mixture wa stirred overnight at room temperature, then washed with water. The methylene chloride layer was extracted with dilute hydrochloric acid and the hydrochloric acid layer retained and basified with sodium hydroxide pellets. The basic solution was extracted with diethyl ether and the ether layer was separated, dried and evaporated in vacuo. The oily residue was dissolved in methylene chloride and chromatographed on a column of 450 g of neutral alumina. After eluting in 400-500 ml portions with a total of 3 liters of ethyl acetate, the column was eluted with 2 liters of methanol-ethyl acetate (1:99) in 4-500 ml portions followed by 2 liters of methanol ethyl acetate (2:98) in 500 ml portions. The desired material had not been completely eluted from the column. The column was allowed to run dry and sectioned. The desired product was extracted from the bottom portion of the column by three times suspending the alumina in methanol-methylene chloride (1:1) and filtering through a sintered glass funnel. The combined filtrate was concentrated in vacuo. The residue, thought to be largely the acetate salt of the product, was partitioned between methylene chloride and dilute sodium hydroxide. The methylene chloride layer was combined with column fractions containing nearly pure product and evaporated in vacuo to give 4 g residual oil (free base of title compound). Earlier less pure column fractions were combined and concentrated and converted to oxalate salt in isopropyl alcohol-isopropyl ether to give 1.5 g of light-beige solid, m.p. 147°-149° C., the oxalate salt.

Analysis of oxalate salt: Calculated for $C_{25}H_{27}N_4O_5F$: C,62.23; H,5.64; N,11.61. Found: C,61.94; H,5.67; N,11.48.

EXAMPLE 29

2-Chloro-N-[2-[[3-(dimethylamino)propyl]phenylamino]-3-pyridinyl]benzamide

To a stirred solution of 9 g (0.033 mole) of $N^2$-[3-(dimethylamino)propyl]-$N^2$-phenyl-2,3-pyridinediamine and 3.9 g (0.038 mole) triethylamine in 75 ml of dry methylene chloride was added dropwise with stirring at 15°-20° C., 6.4 g (0.037 mole) of 2-chlorobenzoyl chloride. After stirring overnight, the reaction mixture was washed with water. The methylene chloride layer was extracted twice with dilute sodium hydroxide solution, washed with water, dried over sodium sulfate and concentrated in vacuo. The residue was triturated in isopropyl ether to give 10 g (74%) of solid. A portion of this solid was recrystallized from isopropyl alcohol-isopropyl ether to give a cream colored solid, m.p. 90°–92° C.

Analysis: Calculated for $C_{23}H_{25}N_4OCl$: C,67.56; H,6.16; N,13.70. Found: C,67.21; H,6.16; N,13.48.

EXAMPLE 30

2-Bromo-N-[2-[[3-dimethylamino)propyl]-phenylamino]-3-pyridinyl]benzamide oxalate[1:1]

To a stirred solution of 9.0 g (0.033 mole) of $N^2$-[3-(dimethylamino)propyl]-$N^2$-phenyl-2,3-pyridinediamine and 4.0 g (0.040 mole) of triethylamine in 100 ml of dry methylene chloride was added dropwise at 15°–20° C., 8.4 g (0.038 mole) of 2-bromobenzoyl chloride. After stirring for 16 hr at room temperature, the reaction mixture was washed with water and then taken through an acid-base extraction procedure. The isolated material was purified by dry column chromatography using two 1"×23" columns of alumina (deactivated with 10% by weight of eluting solvent) in nylon tubing. Each column was developed with 200 ml of a mixture of benzene-acetone (4:1) and sectioned according to $R_f$ values. The sections containing the desired product were extracted by repeated (3×) suspension of the alumina in methyl alcohol-methylene chloride (1:1) and suction filtering through a sintered glass funnel. Concentration of the filtrates gave 6.8 g (38%) of an oily residue. A portion of this was crystallized as the oxalate salt from tetrahydrofuran-isopropyl ether. Recrystallization from isopropyl alcohol-isopropyl ether gave a cream colored solid which melted with decomposition from 140°–146° C. after undergoing a phase change at 135°–140° C.

Analysis: Calculated for $C_{25}H_{27}N_4O_5Br$: C,55.26; H,5.01; N,10.31. Found: C,55.22; H,5.14; N,10.56.

EXAMPLE 31

N-[2-[(N'-Methyl-N'-phenyl)amino]-3-pyridinyl]benzamide fumarate

When in accordance with the procedure of Example 24, $N^2$-methyl-$N^2$-phenyl-2,3-pyridinediamine (free base of Example 20) is reacted with benzoyl chloride, the title compound is obtained.

EXAMPLE 32

N-[2-[(N'-Methyl-N'-(4-chlorophenyl)-amino]-3-pyridinyl]-benzamide

When in accordance with the procedure of Example 24, $N^2$-(4-chlorophenyl)-$N^2$-methyl-2,3-pyridinediamine is reacted with benzoyl chloride, the title compound is obtained.

EXAMPLE 33

When in the procedure of Example 24, equal molar amounts of the following are substituted for $N^2$-[3-(dimethylamino)propyl]-$N^2$-phenyl-2,3-pyridinediamine, $N^2$-(4-morpholinopropyl)-$N^2$-phenyl-2,3-pyridinediamine, $N^2$-(1-piperidinopropyl)-$N^2$-phenyl-2,3-pyridinediamine, $N^2$-(1-pyrrolidinopropyl)-$N^2$-phenyl-2,3-pyridinediamine, and $N^2$-(4-methyl-1-piperazinylpropyl)-$N^2$-phenyl-2,3-pyridinediamine. there are obtained:

(a) N-[2-[[3-(4-morpholino)propyl]phenylamino]-3-pyridinyl]benzamide,
(b) N-[2-[[3-(1-piperidino)propyl]phenylamino]-3-pyridinyl]benzamide,
(c) N-[2-[[3-(1-pyrrolidino)propyl]phenylamino]-3-pyridinyl]benzamide, and
(d) N-[2-[[3-(4-methylpiperazin-1-yl-propyl)]-phenylamino]-3-pyridinyl]benzamide.

EXAMPLE 34a AND b

When in accordance with the procedure of Example 24, equal molar amounts of the following are substituted for benzoyl chloride:

2-thiophenecarbonyl chloride, and
3-thiophenecarbonyl chloride,
there are obtained:

(a) N-[2-[[3-(dimethylamino)propyl]phenylamino]-3-pyridinyl]-2-thiophenecarboxamide, and
(b) N-[2-[[3-(dimethylamino)propyl]phenylamino]-3-pyridinyl]-3-thiophenecarboxamide.

EXAMPLE 35

N-[2-[[3-(Dimethylamino)propyl]phenylamino]-3-pyridinyl]-2-pyridinecarboxamide oxalate[1:1]

A solution of 6.0 g (0.049 mole) of picolinic acid and 24 g (0.2 mole) of thionyl chloride in 20 ml of benzene were refluxed under nitrogen atmosphere for 3 hours. The reaction mixture was concentrated in a rotary evaporator feeding in nitrogen to break the vacuum. Dry benzene (50 ml) was added to the residue and the mixture was again concentrated on a rotary evaporator. The residue (picolinic acid chloride hydrochloride) was taken up into 30 ml methylene chloride, at 10°–20° C., and added to a mixture of 11.0 g (0.041 mole) of $N^2$-[3-(dimethylamino)propyl]-$N^2$-phenyl-2,3-pyridinediamine, 10 g triethylamine, 1 g of powdered molecular sieves and 70 ml of dry methylene chloride. The mixture was stirred for 1.5 hr at room temperature. After further stirring overnight, starting pyridinediamine was still present as indicated by thin-layer chromatography. Additional picolinic acid chloride, prepared as above, (2 g) in 3 g triethylamine was added and the mixture stirred 2 hours at room temperature. Starting pyridinediamine was no longer present. The reaction mixture was filtered and the filtrate was washed in sequence with water, three times with dilute sodium hydroxide (pH=14), water and saturated sodium chloride. The methylene chloride solution was dried over sodium sulfate and concentrated on a rotary evaporator. Weight of the residue was 16 g, predominantly the free base of the title compound. Oxalic acid, 4 g, in isopropyl alcohol was added and 14.1 g (74%) of the oxalate title compound obtained. A portion of the product was recrystallized from isopropyl-alcohol-water and dried overnight at 56° C. in vacuo.

Analysis: Calculated for $C_{24}H_{27}N_5O_5$: C,61.92; H,5.85; N,15.04. Found: C,61.64; H,5.83; N,14.94.

EXAMPLE 36a AND b

When in accordance with the procedure of Example 35, equal molar amounts of the following are substituted for benzoyl chloride:

3-pyridinecarbonyl chloride, and 4-pyridinecarbonyl chloride,
there are obtained:
(a) N-[2-[[3-(dimethylamino)propyl]phenylamino]-3-pyridinyl]-3-pyridinecarboxamide oxalate, and
(b) N-[2-[[3-(dimethylamino)propyl]phenylamino]-3-pyridinyl]-4-pyridinecarboxamide oxalate.

EXAMPLE 37a TO f

When in accordance with the procedure of Example 24, equal molar amounts of the following are substituted for N$^2$-[3-(dimethylamino)propyl]-N$^2$-phenyl-2,3-pyridinediamine:

N-(3-amino-4-methyl-2-pyridinyl)-N',N'-dimethyl-N-phenylpropanediamine,
N-(3-amino-5-methyl-2-pyridinyl)-N',N'-dimethyl-N-phenylpropanediamine,
N-(3-amino-6-methyl-2-pyridinyl)-N',N'-dimethyl-N-phenylpropanediamine,
N-(3-amino-5,6-dimethyl-2-pyridinyl)-N',N'-dimethyl-N-phenylpropanediamine,
N-(3-amino-6-methoxy-2-pyridinyl)-N',N'-dimethyl-N-phenylpropanediamine, and
N-(3-amino-2-methyl-4-pyridinyl)-N',N'-dimethyl-N-phenylpropanediamine, there are obtained:
(a) N-[2-[[3-(dimethylamino)propyl]phenylamino]-4-methyl-3-pyridinyl]benzamide,
(b) N-[2-[[3-(dimethylamino)propyl]phenylamino]-5-methyl-3-pyridinyl]benzamide,
(c) N-[2-[[3-(dimethylamino)propyl]phenylamino]-6-methyl-3-pyridinyl]benzamide,
(d) N-[2-[[3-(dimethylamino)propyl]phenylamino]-5,6-methyl-3-pyridinyl]benzamide,
(e) N-[2-[[3-(dimethylamino)propyl]phenylamino]-6-methoxy-3-pyridinyl]benzamide,
(f) N-[4-[[3-(dimethylamino)propyl]phenylamino]-2-methyl-3-pyridinyl]benzamide.

EXAMPLE 38

N-[2-[[3-(Dimethylamino)propyl]phenylamino]-3-pyridinyl]-2-nitrobenzamide

N$^2$-[3-(Dimethylamino)propyl]-N$^2$-phenyl-2,3-pyridinediamine and 2-nitrobenzoyl chloride were reacted to give the title compound as light yellow solid which was recrystallized from isopropyl alcohol, m.p. 134°–136° C.

Analysis: Calculated for C$_{23}$H$_{25}$N$_5$O$_3$: C,65.86; H,6.01; N,16.69. Found: C,65.87; H,6.14; N,16.66.

EXAMPLE 39

2-Bromo-N-[2-[(4-chlorophenyl)methylamino]-3-pyridinyl]benzamide

To a stirred solution of 7.33 g (0.031 mole) of N$^2$-(4-chlorophenyl)-N$^2$-methyl-2,3-pyridinamine and 3.65 g (0.036 mole) of triethylamine in 50 ml of dry methylene chloride was added dropwise at 10°–15° C., 7.48 g (0.034 mole) of 2-bromobenzoyl chloride. After stirring for 1½ hr at room temperature, the reaction mixture was washed with water. The resulting methylene chloride layer was washed twice with dilute sodium hydroxide followed by water and then dried over sodium sulfate and concentrated in vacuo. The crystalline residue was recrystallized from ethyl acetate-isopropyl ether to give 5.2 g solid. A second crop from the filtrate gave 3.48 g solid for a total yield of 62%. The second crop was recrystallized from benzene-cyclohexane, m.p. 135°–147° C.

Analysis: Calculated for C$_{19}$H$_{15}$N$_3$OBrCl: C,54.76; H,3.63; N,10.08. Found: C,54.75; H,3.62; N,10.29.

EXAMPLE 40

2-Chloro-N-[2-[(4-chlorophenyl)methylamino]-3-pyridinyl]benzamide

To a stirred solution of 6.0 g (0.026 mole) of N$^2$-(4-chlorophenyl)-N$^2$-methyl-2,3-pyridinamine and 3.0 g (0.030 mole) of triethylamine in 50 ml of dry methylene chloride (dried over molecular sieves) was added dropwise at 10°–15° C., 5.0 g (0.028 mole) of 2-chlorobenzoyl chloride. The reaction mixture was stirred for 1½ hr at room temperature then washed with water. The resulting methylene chloride layer was washed in sequence with dilute sodium hydroxide, water, and saturated sodium chloride solution. The methylene chloride layer was dried over sodium sulfate and concentrated in vacuo. The residue was triturated in cyclohexane to give 5.9 g (6%) of solid. A portion of this solid was recrystallized from benzene-cyclohexane using charcoal treatment to give a white flocculent solid, m.p. 117°–119° C.

Analysis: Calculated for C$_{19}$H$_{15}$N$_3$OCl$_2$: C,61.30; H,4.06; N,11.29. Found: C,61.38; H,4.08; N,11.27.

EXAMPLE 41

N-[2-[(4-Chlorophenyl)methylamino]-3-pyridinyl]-2-fluorobenzamide

To a stirred solution of 9.0 g (0.038 mole) of N$^2$-(4-chlorophenyl)-N$^2$-methyl-2,3-pyridinamine in 75 ml of dry methylene chloride was added, dropwise, at 20°–25° C., 6.7 g (0.042 mole) of 2-fluorobenzoyl chloride. After stirring overnight at room temperature, the reaction mixture was washed with water. The resulting methylene chloride layer was washed in sequence twice with dilute sodium hydroxide, water and saturated sodium chloride solution. The methylene chloride solution was concentrated in vacuo. The residue was triturated in isopropyl ether to give 12 g (88%) solid. Recrystallization from isopropyl alcohol-isopropyl ether gave an off-white solid, m.p. 76°–78° C.

Analysis: Calculated for C$_{19}$H$_{15}$N$_3$OClF: C,64.14; H,4.25; N,11.81. Found: C,64.03; H,4.24; N,11.91.

EXAMPLE 42

N-[2-[(4-Chlorophenyl)methylamino]-3-pyridinyl]-2-nitrobenzamide

To a stirred solution of 9.0 g (0.0385 mole) of N$^2$-(4-chlorophenyl)-N$^2$-methyl-2,3-pyridinamine and 4.7 g (0.0462 mole) of triethylamine in 75 ml of dry methylene chloride was added dropwise at 15°–25° C., 8.2 g (0.0443 mole) of 2-nitrobenzoyl chloride. After stirring for 19 hr at room temperature, the reaction mixture was washed with water. The resulting methylene chloride layer was extracted in sequence twice with dilute sodium hydroxide, water and saturated sodium chloride solution. The methylene chloride solution was concentrated in vacuo. The residue was taken up in hot ethanol. The alcohol solution was filtered and cooled to give 11.5 g (78%) of crystalline solid. Recrystallization from ethanol gave a light-yellow solid, m.p. 145°–147° C.

Analysis: Calculated for C$_{19}$H$_{15}$N$_4$O$_3$Cl: C,59.61; H,3.95; N,14.64. Found: C,59.59; H,3.85; N,14.75.

EXAMPLE 43

2-Bromo-N-[2-(methylphenylamino)-3-pyridinyl]benzamide $N^2$-Methyl-$N^2$-phenyl-2,3-pyridinediamine and 2-bromobenzoyl chloride were reacted to give the title compound which was recrystallized from isopropyl alcohol to give an off-white solid, m.p. 144°–146° C.

Analysis: Calculated for $C_{19}H_{16}N_3OBr$: C,59.70; H,4.22; N,10.99. Found: C,59.79; H,4.37; N,10.83.

EXAMPLE 44

2-Chloro-N-[2-(methylphenylamino)-3-pyridinyl]benzamide $N^2$-Methyl-$N^2$-phenyl-2,3-pyridinediamine and 2-chlorobenzoyl chloride were reacted to give the title compound as white solid, m.p. 145°–146° C.

Analysis: Calculated for $C_{19}H_{16}N_3OCl$: C,67.56; H,4.77; N,12.44. Found: C,67.49; H,4.77; N,12.40.

EXAMPLE 45

2-Fluoro-N-[2-(methylphenylamino)-3-pyridinyl]benzamide $N^2$-Methyl-$N^2$-phenyl-2,3-pyridinediamine and 2-fluorobenzoyl chloride were reacted to give the title compound, which was recrystallized from isopropyl ether as beige solid, m.p. 84°–86° C.

Analysis: Calculated for $C_{19}H_{16}N_3OF$: C,71.02; H,5.02; N,13.08. Found: C,71.01; H,5.00; N,13.03.

EXAMPLE 46

N-[2-[(4-Chlorophenyl)methylamino]-3-pyridinyl]-2-pyridinecarboxamide $N^2$-(4-Chlorophenyl)-$N^2$-methyl-2,3-pyridinediamine and picolinic acid chloride were reacted as in Example 35 to give the title compound, in 80% yield, which was then isolated and recrystallized from isopropyl alcohol, m.p. 123°–125° C.

Analysis: Calculated for $C_{18}H_{15}N_4OCl$: C,63.81; H,4.46; N,16.54. Found: C,63.60; H,4.43; N,16.50.

EXAMPLE 47

N,N-Dimethyl-6-phenyl-11H-pyrido[2,3-b][1,4]benzodiazepine-11-propanamine fumarate [1:1]

N-[2-[[3-(Dimethylamino)propyl]phenylamino]-3-pyridinyl]benzamide, 4.1 g (0.01 mole), was mixed with 5.70 ml of phosphorus oxychloride and refluxed for 7 hr followed by stirring overnight. Excess phosphorus oxychloride was removed by evaporation under reduced pressure and the residue dissolved in water. The solution was cooled in an ice bath and methylene chloride added with stirring to form a second layer. Aqueous 50% sodium hydroxide was added in an amount to make the aqueous layer strongly basic. The methylene chloride extract was separated and washed once with sodium chloride solution. The aqueous layer was extracted a second time with methylene chloride and the methylene chloride layer was separated and washed with saturated sodium chloride solution. The methylene chloride extracts were combined and dried over sodium sulfate and evaporated to give a black oil, predominantly the free base of the title compound. The oil was dissolved in 20 ml of isopropyl alcohol and 1.2 g (0.01 mole) of fumaric acid in 40 ml of isopropyl alcohol was added. The solution was treated with activated charcoal and filtered. The volume was reduced and isopropyl ether was added. The product did not crystallize and a brown oil remained. The brown oil was dissolved in 15 ml of hot tetrahydrofuran. Ethyl acetate was added slowly in small portions. Crystallization occurred with stirring. After about 80 ml of ethyl acetate had been added, the suspension was stirred for 1 hr and filtered, washing with ethyl acetate. Yield of product after drying was 3.2 g (68%). On recrystallizing from ethanol and drying under high vacuum, the product melted, 171°–173° C.

EXAMPLE 48a TO b

When in accordance with the procedure of Example 47, equal molar amounts of the following are substituted for N-[2-[[3-(dimethylamino)propyl]phenylamino]-3-pyridinyl]benzamide:

N-[2-[[3-(dimethylamino)ethyl]phenylamino]-3-pyridinyl]benzamide, or

N-[2-[[3-(dimethylamino)butyl]phenylamino]-3-pyridinyl]benzamide, there are obtained:

(a) N,N-dimethyl-6-phenyl-11H-pyrido[2,3-b][1,4]benzodiazepine-11-ethanamine fumarate, and (b) N,N-dimethyl-6-phenyl-11H-pyrido[2,3b][1,4]benzodiazepine-11-butanamine fumarate.

EXAMPLE 49

6-(2-Fluorophenyl)-N,N-dimethyl-11H-pyrido[2,3-b][1,4]benzodiazepine-11-propanamine A solution of 8.5 g (0.022 mole) of N-[2-[[3-(dimethylamino)propyl]phenylamino]-3-pyridinyl]-2-fluorobenzamide in 26 g (0.173 mole) of phosphorus oxychloride was refluxed under nitrogen atmosphere for 16 hr. The cooled reaction mixture was poured over ice, diluted with water, and extracted twice with diethyl ether. The acidic portion was made basic with sodium hydroxide pellets, cooled with ice and extracted twice with methylene chloride. The combined methylene chloride layers were washed in sequence with water and saturated sodium chloride, dried over sodium sulfate and concentrated in vacuo. The residue was crystallized from isopropyl alcohol-isopropyl ether using charcoal treatment to yield 3.2 g (39%) of a bright-yellow solid, m.p. 92°–94° C.

Analysis: Calculated for $C_{23}H_{23}N_4F$: C,73.77; H,6.19; N,14.96. Found: C,73.67; H,6.20; N,14.82.

EXAMPLE 50

6-(2-Chlorophenyl)-N,N-dimethyl-11H-pyrido[2,3-b][1,4]benzodiazepine-11-propanamine A solution of 7.0 g (0.017 mole) of 2-chloro-N-[2-[[3-(dimethylamino)propyl]phenylamino]-3-pyridinyl]benzamide and 10.5 g (0.069 mole) of phosphorus oxychloride in 5 ml of 1,1,2,2-tetrachlorethane was heated under nitrogen atmosphere at 110°–115° C. for 16 hr. The cooled reaction mixture was poured into ice and 10 ml of dilute hydrochloric acid added. The mixture was extracted twice with petroleum ether. The acidic portion was made basic with sodium hydroxide pellets and thereafter extracted twice with methylene chloride. The combined methylene chloride extracts were washed with water, dried over sodium sulfate and concentrated in vacuo. The residue was crystallized from isopropyl ether yielding 6.0 g (90%) of material. Recrystallization from isopropyl alcohol-isopropyl ether gave a yellow solid, m.p. 104°–105.6° C.

Analysis: Calculated for $C_{23}H_{23}N_4Cl$: C,70.67; H,5.93; N,14.33. Found: C,70.44; H,5.95; N,14.20.

EXAMPLE 51

6-(2-Bromophenyl)-N,N-dimethyl-11H-pyrido[2,3-b][1,4]benzodiazepine-11-propanamine A solution of 7.0 g (0.015 mole) of 2-bromo-N-[2-[[3-(dimethylamino)propyl]phenylamino]-3-pyridinyl]benzamide and 19 g (0.124 mole) of phosphorus oxychloride was refluxed under nitrogen atmosphere for 16 hr. The cooled reaction mixture was poured over ice and the solution extracted twice with diethyl ether. The acidic layer was made basic with dilute sodium hydroxide and extracted with methylene chloride. The methylene chloride layer was washed with water, dried over sodium sulfate and concentrated in vacuo. The residue was dissolved in benzene, boiled with charcoal and filtered. The filtrate was concentrated in vacuo. Crystallization from isopropyl ether gave 3 g (46%) of a lime green solid, m.p. 96°–98° C.

Analysis: Calculated for $C_{23}H_{23}N_4Br$: C,63.45; H,5.32; N,12.87. Found: C,63.49; H,5.34; N,12.89.

EXAMPLE 52

N,N-Dimethyl-6-(2-nitrophenyl)-11H-pyrido[2,3-b[[1,4]benzodiazepine-11-propanamine monohydrochloride Following the procedure of Example 51, N-[2-[[3-(dimethylamino)propyl]phenylamino]-3-pyridinyl]-2-nitrobenzamide was cyclized to the free base of title compound with phosphorus oxychloride and thereafter converted to the hydrochloride by reacting with ethereal hydrogen chloride. Recrystallized from isopropyl alcohol, the yellow solid melted at 239°–240° C.

Analysis: Calculated for $C_{23}H_{24}N_5O_2Cl$: C,63.08; H,5.52; N,15.99. Found: C,62.75; H,5.67; N,15.75.

EXAMPLE 53a TO l

When in accordance with the procedure of Example 47, equal molar amounts of the following are substituted for N-[2-[[3-(dimethylamino)propyl]phenylamino]-2-pyridinyl]benzamide:

N-[2-[[3-(dimethylamino)propyl](4-methylphenyl)amino]-3-pyridinyl]benzamide,
N-[2-[[3-(dimethylamino)propyl](3-methoxyphenyl)amino]-3-pyridinyl]benzamide,
4-chloro-N-[2-[[3-(dimethylamino)propyl]phenylamino]-3-pyridinyl]benzamide,
N-[3-[[3-(dimethylamino)propyl]phenylamino]-4-pyridinyl]benzamide,
N-[3-[[3-(dimethyl)propyl](4-methylphenyl)amino]-4-pyridinyl]benzamide,
N-[5-[[3-(dimethylamino)propyl]phenylamino]-2-methoxy-4-pyridinyl]benzamide,
N-[4-[[3-(dimethylamino)propyl]phenylamino]-3-pyridinyl]benzamide,
N-[3-[[3-(dimethylamino)propyl]phenylamino]-2-pyridinyl]benzamide,
1,3-dihydro-N-[2-[[3-(1,3-dioxo-2H-isoindol-2-yl)propyl]phenylamino]-3-pyridinyl]benzamide,
[3-[[3-(benzoylamino)-2-pyridinyl]phenylamino]propyl]methylcarbamic acid 1,1-dimethylethyl ester,
N-[3-[[3-(dimethylamino)propyl](4-chlorophenyl)amino]-2-pyridinyl]benzamide, and
N-[3-[[3-(dimethylamino)propyl](4-bromophenyl)amino]-2-pyridinyl]benzamide,
there are obtained:

(a) N,N-dimethyl-8-methyl-6-phenyl-11H-pyrido[2,3-b][1,4]benzodiazepine-11-propanamine, fumarate,
(b) N,N-dimethyl-9-methoxy-6-phenyl-11H-pyrido[2,3-b][1,4]benzodiazepine-11-propanamine, fumarate,
(c) N,N-dimethyl-6-(4-chlorophenyl)-11H-pyrido[2,3-b][1,4]benzodiazepine-11-propanamine, fumarate,
(d) N,N-dimethyl-6-phenyl-11H-pyrido[3,4-b][1,4]benzodiazepine-11-propanamine fumarate,
(e) N,N-dimethyl-8-methyl-6-phenyl-11H-pyrido[3,4-b][1,4]benzodiazepine-11-propanamine fumarate,
(f) N,N-dimethyl-3-methoxy-6-phenyl-11H-pyrido[3,4-b][1,4]benzodiazepine-11-propanamine fumarate,
(g) N,N-dimethyl-10-phenyl-5H-pyrido[4,3-b][1,4]benzodiazepine-5-propanamine fumarate,
(h) N,N-dimethyl-10-phenyl-5H-pyrido[3,2-b][1,4]benzodiazepine-5-propanamine fumarate,
(i) 11-[3-(1,3-dihydro-1,3-dioxo-2H-isoindol-2-yl)propyl]-6-phenyl-11H-pyrido[2,3-b][1,4]benzodiazepine,
(j) N-methyl-N-[3-(11H-pyrido[2,3-b][1,4]benzodiazepine-11-yl)propyl]carbamic acid methyl ester,
(k) N,N-dimethyl-6-phenyl-8-chloro-11H-pyrido[2,3-b][1,4]benzodiazepine-11-propanamine fumarate, and
(l) N,N-dimethyl-6-phenyl-8-bromo-11H-pyrido[2,3-b][1,4]benzodiazepine-11-propanamine fumarate.

EXAMPLE 54a TO d

When in accordance with the procedure of example 51, equal molar amounts of the following are substituted for 2-bromo-N-[2-[[3-(dimethylamino)propyl]phenylamino]-3-pyridinyl]benzamide, N-[2-[[3-(4-morpholinyl)propyl]phenylamino]-3-pyridinyl]benzamide,
N-[2-[[3-(1-piperidinyl)propyl]phenylamino]-3-pyridinyl]benzamide,
N-[2-[[3-(1-pyrrolidinyl)propyl]phenylamino]-3-pyridinyl]benzamide, and
N-[2-[[3-(4-methyl-1-piperizinyl)propyl]phenylamino]-3-pyridinyl]benzamide,
there are obtained:

(a) 11-[3-(4-morpholinyl)propyl]-6-phenyl-11H-pyrido[2,3-b][1,4]benzodiazepine,
(b) 6-phenyl-11-[3-(1-piperidinyl)propyl]-11H-pyrido[2,3-b][1,4]benzodiazepine,
(c) 6-phenyl-11-[3-(1-pyrrolidinyl)propyl]-11H-pyrido[2,3-b][1,4]benzodiazepine, and
(d) 6-phenyl-11-[3-(4-methyl-1-piperazinyl)propyl]-11H-pyrido[2,3-b][1,4]benzodiazepine.

EXAMPLE 55a AND b

When in accordance with the procedure of Example 51, equal molar amounts of the following are substituted for 2-bromo-N-[2-[[3-(dimethylamino)propyl]phenylamino]-3-pyridinyl]benzamide, N-[2-[[3-(dimethylamino)propyl]phenylamino]-3-pyridinyl]-2-thiophenecarboxamide, and
N-[2-[3-(dimethylamino)propyl]phenylamino]-3-thiophenecarboxamide,
there are obtained:
(a) 11-[3-(dimethylamino)propyl]-6-(2-thienyl)-11H-pyrido[2,3-b][1,4]benzodiazepine,
(b) 11-[3-(dimethylamino)propyl]-6-(3-thienyl)-11H-pyrido[2,3-b][1,4]benzodiazepine.

EXAMPLE 56a TO c

When in accordance with the procedure of Example 51, equal molar amounts of the following are substituted for 2-bromo-N-[2-[[3-dimethylamino)propyl]-phenylamino]-3-pyridinyl]benzamide, N-[2-[[3-(dimethylamino)propyl]phenylamino]-3-pyridinyl]-2-pyridinecarboxamide, N-[2-[[3-(dimethylamino)propyl]phenylamino]-3-pyridinyl]-3-pyridinecarboxamide, and N-[2-[[3-(dimethylamino)propyl]phenylamino]-3-pyridinyl]-4-pyridinecarboxamide, there are obtained:

(a) 11-[3-(dimethylamino)propyl]-6-(2-pyridinyl)-11H-pyrido[2,3-b][1,4]benzodiazepine, (b) 11-[3-(dimethylamino)propyl]-6-(3-pyridinyl)-11H-pyrido[2,3-b][1,4]benzodiazepine, and (c) 11-[3-(dimethylamino)propyl]-6-(4-pyridinyl)-11H-pyrido[2,3-b][1,4]benzodiazepine.

EXAMPLE 57a TO f

When in accordance with the procedure of Example 47, equal molar amounts of the following are substituted for N-[2-[[3-(dimethylamino)propyl]phenylamino]-3-pyridinyl]benzamide:

N-[2-[[3-(dimethylamino)propyl]phenylamino]-4-methyl-3-pyridinyl]benzamide,

N-[2-[[3-(dimethylamino)propyl]phenylamino]-5-methyl-3-pyridinyl]benzamide,

N-[2-[[3-(dimethylamino)propyl]phenylamino]-6-methyl-3-pyridinyl]benzamide,

N-[2-[[3-(dimethylamino)propyl]phenylamino]-5,6-methyl-3-pyridinyl]benzamide,

N-[2-[[3-(dimethylamino)propyl]phenylamino]-6-methoxy-3-pyridinyl]benzamide, and N-[2-[[3-(dimethylamino)propyl]phenylamino]-2-methyl-4-pyridinyl]benzamide, there are obtained:

(a) N,N-dimethyl-4-methyl-6-phenyl-11H-pyrido[2,3-b][1,4]benzodiazepine-11-propanamine fumarate, (b) N,N-dimethyl-3-methyl-6-phenyl-11H-pyrido[2,3-b][1,4]benzodiazepine-11-propanamine fumarate, (c) N,N-dimethyl-2-methyl-6-phenyl-11H-pyrido[2,3-b][1,4]benzodiazepine-11-propanamine fumarate, (d) N,N-dimethyl-2,3-dimethyl-6-phenyl-11H-pyrido[2,3-b][1,4]benzodiazepine-11-propanamine fumarate, (e) N,N-dimethyl-2-methoxy-6-phenyl-11H-pyrido[2,3-b][1,4]benzodiazepine-11-propanamine fumarate, and (f) N,N-dimethyl-1-methyl-10-phenyl-5H-pyrido[4,3-b][1,4]benzodiazepine-5H-propanamine fumarate.

EXAMPLE 58

8-Chloro-6-(2-chlorophenyl)-11-methyl-11H-pyrido[2,3-b][1,4]benzodiazepine

A mixture of 3.7 g (0.0099 mole) of 2-chloro-N-[2-[(4-chlorophenyl)methylamino]-3-pyridinyl]benzamide and 12 g (0.0796 mole) of phosphorus oxychloride in 10 ml of 1,1,2,2-tetrachloroethane was heated at 110° C. under nitrogen atmosphere for 16 hr. The cooled reaction mixture was poured over ice, made basic with dilute sodium hydroxide and extracted twice with methylene chloride. The combined methylene chloride extract was washed with water, dried over sodium sulfate and concentrated in vacuo at 100° C. The residue was triturated in isopropyl ether which gave on filtration 2.5 g (71%) solid. The residue was twice recrystallized from isopropyl alcohol-isopropyl ether using charcoal treatment to give a yellow solid, m.p. 150°–152° C.

Analysis: Calculated for $C_{19}H_{13}N_3Cl_2$: C,64.42; H,3.70; N,11.86. Found: C,64.41; H,3.70; N,11.98.

EXAMPLE 59

8-Chloro-6-(2-fluorophenyl)-11-methyl-11H-pyrido[2,3-b][1,4]benzodiazepine

A mixture of 8.5 g (0.024 mole) of N-[2-[(4-chlorophenyl)methylamino]-3-pyridinyl]-2-fluorobenzamide and 37 g (0.242 mole) of phosphorus oxychloride in 10 ml of 1,1,2,2-tetrachloroethane was heated under nitrogen atmosphere at 110° C. for 26 hr. The cooled reation mixture was poured over ice, made basic with dilute sodium hydroxide and extracted twice with methylene chloride. The combined methylene chloride extract was washed with water, dried over sodium sulfate and concentrated in vacuo. The residue was twice recrystallized from isopropyl ether to give 4.5 g (55%) of yellow flocculent solid, m.p. 136°–138° C.

Analysis: Calculated for $C_{19}H_{13}N_3FCl$: C,67.56; H,3.88; N,12.44. Found: C,67.45; H,3.86; N,12.52.

EXAMPLE 60

6-(2-Bromophenyl)-8-chloro-11-methyl-11H-pyrido[2,3-b][1,4]benzodiazepine

A solution of 5.0 g (0.012 mole) of 2-bromo-N-[2-[4-chlorophenyl)methylamino]-3-pyridinyl]benzamide and 5.0 g (0.049 mole) of phosphorus oxychloride in 75 ml of 1,1,2,2-tetrachloroethane was heated overnight under nitrogen atmosphere at 105° C. The cooled reaction mixture was poured over ice, made basic with sodium hydroxide (15%) and the layers separated. The organic layer was washed twice with sodium hydroxide (15%) and once with water, dried over sodium sulfate and concentrated in vacuo at 99° C. The residue was crystallized from pet. ether (30°–60° C.). Recrystallization from isopropyl ether gave 3 g (63%) of bright yellow solid, m.p. 121°–123° C.

Analysis: Calculated for $C_{19}H_{13}N_3BrCl$: C,57.24; H,3.29; N,10.54. Found: C,57.31; H,3.26; N,10.62.

EXAMPLE 61

8-Chloro-11-methyl-6-(2-nitrophenyl)-11H-pyrido[2,3-b][1,4]benzodiazepine

A mixture of 9.0 g (0.024 mole) of N-[2-[(4-chlorophenyl)methylamino]-3-pyridinyl]-2-nitrobenzamide and 24.4 g (0.159 mole) of phosphorus oxychloride in 5 ml of 1,1,2,2-tetrachloroethane was heated under nitrogen atmosphere at 110° C. for 20 hr. The cooled reaction mixture was poured into ice, made basic with dilute sodium hydroxide and extracted with methylene chloride. The combined methylene chloride extract was washed with water, dried over sodium sulfate and concentrated in vacuo. The residue was triturated in isopropyl alcohol-isopropyl ether mixture. The solid, collected by filtration and dried, was recrystallized from ethyl alcohol using charcoal treatment to give 2.3 g (26%) of a yellow-gold solid, m.p. 165°–166° C.

Analysis: Calculated for $C_{19}H_{13}N_4O_2Cl$: C,62.56; H,3.59; N,15.36. Found: C,62.32; H,3.56; N,15.36.

EXAMPLE 62

6-(2-Chlorophenyl)-11-methyl-11H-pyrido[2,3-b][1,4]benzodiazepine

Following the procedure of example 58, 2-chloro-N-[2-(methylphenylamino)-3-pyridinyl]benzamide was cyclized to the title compound with phosphorus oxychloride and isolated, recrystallizing from isopropyl alcohol as yellow solid, m.p. 131.5°–133° C.

Analysis: Calculated for $C_{19}H_{14}N_3Cl$: C,71.36; H,4.41; N,13.14. Found: C,71.29H,4.42; N,13.26.

EXAMPLE 63

6-(2-Bromophenyl)-11-methyl-11H-pyrido[2,3-b][1,4]benzodiazepine

Following the procedure of example 58, 2-bromo-N-[2-(methylphenylamino)-3-pyridinyl]benzamide was cyclized to the title compound and thereafter isolated, recrystallizing from isopropyl alcohol as dark mustard solid, m.p. 139°–140° C.

Analysis: Calculated for $C_{19}H_{14}N_3Br$: C,62.65; H,3.87; N,11.54. Found: C,62.75; H,3.90; N,11.62.

EXAMPLE 64

6-(2-Fluorophenyl)-11-methyl-11H-pyrido[2,3-b][1,4]benzodiazepine

Following the procedure of example 58, 2-fluoro-N-[2-(methylphenylamino)-3-pyridinyl]benzamide was cyclized to the title compound and thereafter isolated, recrystallizing from isopropyl alcohol as yellow solid, m.p. 140°–142° C.

Analysis: Calculated for $C_{19}H_{14}N_3F$: C,75.23; H,4.65; N,13.85. Found: C,75.20; H,4.74; N,13.68.

EXAMPLE 65

11-Methyl-6-phenyl-11H-pyrido[2,3-b][1,4]benzodiazepine

Following the procedure of example 58, N-[2-[phenylmethylamino]-3-pyridinyl]benzamide and phosphorus oxychloride are heated together and the title compound is isolated.

EXAMPLE 66

8-Chloro-11-methyl-6-phenyl-11H-pyrido[2,3-b][1,4]benzodiazepine

Following the procedure of Example 58, N-[2-[4-chlorophenyl)methylamino]-3-pyridinyl]benzamide and phosphorus oxychloride are heated together and the title compound is isolated.

EXAMPLE 67

(Pyrido[1,4]benzodiazepine without complete purification or isolation of intermediates)

Process For Preparation of N,N-Dimethyl-6-phenyl-11H-pyrido[2,3-b][1,4]benzodiazepine-11-propanamine fumarate[1:1]

(a) Step 1—Preparation of Crude 3-nitro-N-phenyl-2-pyridinamine.

To 955 g (10.3 moles) of aniline heated to 127° C. was added 1,300 g of 2-chloro-3-nitropyridine in small portions over a period of 1.5 hr. The mixture was heated to 140°–150° C. for 1 hr. NMR and mass spec showed no starting 2-chloro-3-nitropyridine was present. The hot slurry was poured into 10 l. of ice water containing 175 g of potassium carbonate and 130 g of 50% sodium hydroxide. The product precipitated as dark chunks. Solid was collected and washed with 6 l. of water and suction filtered, dried at 140° F. overnight. Product was pulverized in a Waring blender and dried for 4 hr at 140° C., weight of dark colored solid was 1,800 g=crude 3-nitro-N-phenyl-2-pyridinamine.

(b) Step 2—Preparation of Solution of Crude N,N-Dimethyl-N'-(3-nitro-2-pyridinyl)-N'-phenyl-propanediamine.

The crude product from step 1, 1800 g (assumed to contain 7.9 moles) of 3-nitro-N-phenyl-2-pyridinamine was mixed with 1,787 g (11.8 moles) of 3-dimethylaminopropyl chloride, 3.24 liters of toluene, 252.9 g (0.79 moles) of tetrabutylammonium bromide and 4,175 g (58.94 moles) of 50% sodium hydroxide. The mixture was heated and at 94° C. the mixture became thick and began foaming with vigorous reflux. Heating was temporarily discontinued and then started after 15 min to reflux at 104° C. for 2 hr. Mass spec. showed the reaction was complete. The mixture was allowed to cool on standing and 3 liters of water was added with stirring. The aqueous layer was extracted with 3 liters of toluene. The toluene layers were combined and dried by stirring with anhydrous sodium sulfate. The mixture was filtered through a celite bed on a medium porosity funnel separating out a black oily residue on the funnel. The toluene solution was concentrated to yield 2,300 g (97%) of crude N,N-dimethyl-N'-(3-nitro-2-pyridinyl)-N-phenylpropanediamine as heavy black oil.

(c) Step 3—Preparation of Crude $N^2$-[3-(dimethylamino)propyl]-$N^2$-phenyl-2,3-pyridinediamine.

The 2300 g crude product from step 2 assumed to contain 7.67 moles of N,N-dimethyl-N'-(3-nitro-2-pyridinyl)-N-phenylpropanediamine was mixed with 346.6 g (8.67 moles) of sodium hydroxide pellets and 17.4 liters of 150 proof ethanol. To the mixture was added in small portions over a period of 1 hr, 2300 g (34.94 moles) of zinc powder. The temperature gradually rose to reflux (82° C.) during addition of zinc and refluxing was continued 1.5 hr after addition was complete. The mixture was filtered on a celite bed, washing the cake twice with about 4 liters of hot ethanol each time. The filtrate was concentrated to remove most of the ethanol and the residue was dissolved in 3 liters of methylene chloride. The methylene chloride solution was washed twice with 2-liter portions of water. The wash water was then extracted with one liter of methylene chloride. Methylene chloride solutions were combined and dried over anhydrous sodium sulfate overnight and filtered, washing the cake with 1.6 l. of methylene chloride.

(d) Step 4—Preparation of Crude N-[2-[[3-(dimethylamino)propyl]phenylamino]-3-pyridinyl]benzamide.

To the stirred methylene chloride solution from step 3 comprised of an assumed 2,071 g (7.67 moles) of $N^2$-[3-(dimethylamino)propyl]-$N^2$-phenyl-2,3-pyridinediamine in 5.6 liters of methylene chloride was added 1077.5 g (884 ml; 7.67 moles) of benzoyl chloride in a fine stream allowing the temperature to rise to reflux. The addition period was 45 min and stirring at ambient temperature continued for 1 hr. NMR analysis indicated a 2:1 ratio of amine to benzoyl chloride remained. An additional 442 ml (3.835 moles) of benzoyl chloride was added and stirring continued for 1.5 hr. The reaction mixture was extracted twice with 2 liter portions of 3N hydrochloric acid and the acidic layers were separated, combined and mixed with 4 liters of toluene and chilled to 15° C. The mixture was basified to pH 9–10 with about 2.5 kg of 50% sodium hydroxide. The toluene layer was separated and washed with about 2 liters of water. The aqueous solutions were combined and extracted with 2 liters of toluene. This toluene layer was washed with water and combined with the main toluene solution. The resulting toluene solution was dried over molecular seives, filtered and concentrated to yield 2,435 g of heavy black oil.

(e) Step 5—Preparation of N,N-Dimethyl-6-phenyl-11H-pyrido[2,3-b][1,4]benzodiazepine-11-propanamine fumarate.

The black oil (2400 g) from step 5 containing the crude N-[2-[[3-(dimethylamino)propyl]phenylamino]-3-pyridinyl]benzamide (approx. 6.42 moles) was mixed gradually by stirring and cooling (not over 55° C.) with 4,921 g of phosphorus oxychloride and the mixture was heated to reflux for 1.75 hr. The mixture was washed by extracting (stirring) three times with 9.5 liter portions of hot toluene, decanting the toluene layer each time. The residue was dissolved by refluxing in 10 liters of methylene chloride for one hr. The methylene chloride solution was basified by slow addition of 6.4 kg of 50% potassium carbonate with cooling. The aqueous layer was separated and extracted with 2 liters of methylene chloride. The methylene chloride layers were combined and stirred with molecular seives for ½ hr. After filtration, the methylene chloride layer solution was evaporated at atmospheric pressure to a pot temperature of 66° C. To the residue was added 14 liters of hot isopropyl ether and a black tarry gum precipitated. The mixture was heated to 67° C. and filtered through 4.75 kg of fluorisil, washing the cake with 2 liters of hot isopropyl ether followed by 6 liters of acetone. The filtrate was treated with Norite "A" and filtered successively through medium and fine porosity funnels. The filtrate was concentrated under reduced pressure and finally at high vacuum to give 911.1 g red oil. The red oil was dissolved in 2 liters of acetone with heat and to this solution was added 297.2 g (2.56 moles) of fumaric acid and 644 ml of acetone. The mixture was heated to reflux to dissolve, stirred and cooled to room temperature and then refrigerated overnight. Filtration and drying gave 1,025 g solid. A portion recrystallized from acetone-dimethyl ether gave yellow solid, m.p. 169°–171° C.

Analysis: Calculated for $C_{27}H_{28}N_4O_4$: C,68.63; H,5.97; N,11.85. Found: C,68.38; H,5.99; N,11.91.

TABLE 1

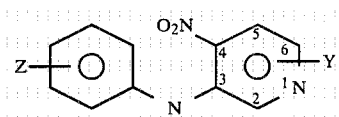

| Example No. | R | Y | Z | Salt |
|---|---|---|---|---|
| 1 | H | H | H | — |
| 2 (a) | H | H | 4-CH₃ | — |
| 2 (b) | H | H | 3-OCH₃ | — |
| 2 (c) | H | H | 4-Cl | — |
| 2 (d) | H | H | 4-Br | — |
| 3 (a) | H | 5-OCH₃ | H | — |
| 5 (a) | H | 4-CH₃ | H | — |
| 5 (b) | H | 5-CH₃ | H | — |
| 5 (c) | H | 6-CH₃ | H | — |
| 5 (d) | H | 5,6-(CH₃)₂ | H | — |
| 5 (e) | H | 6-OCH₃ | H | — |
| 6 | —CH₃ | H | H | HCl |
| 7 | —CH₃ | H | 4-Cl | — |
| 8 | —(CH₂)₃N—(CH₃)₂ | H | H | fumarate |
| 9 (a) | —(CH₂)₃N—(CH₃)₂ | H | 4-CH₃ | fumarate |
| 9 (b) | —(CH₂)₃N—(CH₃)₂ | H | 3-OCH₃ | fumarate |
| 9 (c) | —(CH₂)₃N—(CH₃)₂ | 5-OCH₃ | H | fumarate |
| 9 (i) | —(CH₂)₃N—(CH₃)₂ | H | 4-Cl | fumarate |
| 9 (j) | —(CH₂)₃N—(CH₃)₂ | H | 4-Br | fumarate |
| 10 | —(CH₂)₃—(1-phthalimido) | H | H | — |
| 11 | —(CH₂)₃Cl | H | H | fumarate |
| 12 | —(CH₂)₃N(CH₃)₂ | H | H | — |
| 13 (a) | —(CH₂)₂N—(CH₃)₂ | H | H | fumarate |
| 13 (b) | —(CH₂)₄N—(CH₃)₂ | H | H | fumarate |
| 14 (a) | —(CH₂)₃—(4-morpholinyl) | H | H | fumarate |
| 14 (b) | —(CH₂)₃—(1-piperidinyl) | H | H | fumarate |
| 14 (c) | —(CH₂)₃—(1-pyrrolidinyl) | H | H | fumarate |
| 14 (d) | —(CH₂)₃—(4-methyl-1-piperazinyl) | H | H | fumarate |
| 15 (a) | —(CH₂)₃N—(CH₃)₂ | 4-CH₃ | H | — |
| 15 (b) | —(CH₂)₃N—(CH₃)₂ | 5-CH₃ | H | — |
| 15 (c) | —(CH₂)₃N—(CH₃)₂ | 6-CH₃ | H | — |
| 15 (d) | —(CH₂)₃N—(CH₃)₂ | 5,6-(CH₃)₂ | H | — |
| 15 (e) | —(CH₂)₃N—(CH₃)₂ | 6-OCH₃ | H | — |
| 67 (a) | H | H | H | — |
| 67 (b) | —(CH₂)₃N—(CH₃)₂ | H | H | — |

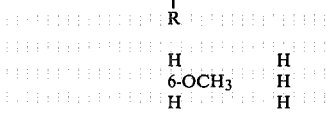

| Example No. | R | Y | Z | Salt |
|---|---|---|---|---|
| 3 (b) | H | H | H | — |
| 3 (c) | H | 6-OCH₃ | H | — |
| 4 | H | H | H | — |
| 9 (d) | —(CH₂)₃N(CH₃)₂ | H | H | fumarate |
| 9 (e) | —(CH₂)₃N(CH₃)₂ | H | 4-CH₃ | fumarate |
| 9 (f) | —(CH₂)₃N(CH₃)₂ | 6-OCH₃ | H | fumarate |

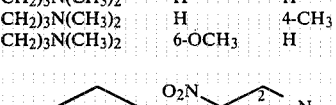

| Example No. | R | Y | Z | Salt |
|---|---|---|---|---|
| 3 (d) | H | H | H | — |
| 5 (f) | H | 2-CH₃ | H | — |
| 9 (g) | —(CH₂)₃N(CH₃)₂ | H | H | fumarate |
| 15 (f) | —(CH₂)₃N(CH₃)₂ | 2-CH₃ | H | fumarate |

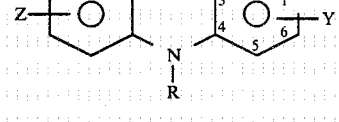

| Example No. | R | Y | Z | Salt |
|---|---|---|---|---|
| 3 (e) | H | H | H | — |
| 9 (h) | —(CH₂)₃N(CH₃)₂ | H | H | fumarate |

TABLE 2

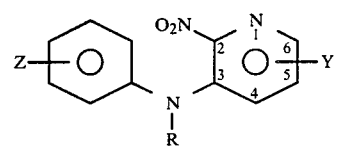

| Example No. | R | Y | Z | Salt |
|---|---|---|---|---|
| 16 | —(CH₂)₂N(CH₃)₂ | H | H | — |
| 17 | —(CH₂)₃N(CH₃)₂ | H | H | 2 HCl |
| 18(a) | —(CH₂)₃N(CH₃)₂ | H | 4-CH₃ | — |
| 18(b) | —(CH₂)₃N(CH₃)₂ | H | 3-OCH₃ | — |
| 18(c) | —(CH₂)₃N(CH₃)₂ | 5-OCH₃ | H | — |
| 18(d) | —(CH₂)₂N(CH₃)₂ | H | H | — |
| 18(e) | —(CH₂)₄N(CH₃)₂ | H | H | — |
| 18(k) | —(CH₂)₃N(CH₃)₂ | H | 4-Cl | — |
| 18(l) | —(CH₂)₃N(CH₃)₂ | H | 4-Br | — |
| 19 | —(CH₂)₃N—(1- | H | H | — |

TABLE 2-continued

| Example No. | R | Y | Z | Salt |
|---|---|---|---|---|
| 20 | —CH₃ (phthalimido) | H | H | HCl |
| 21 | —CH₃ | H | 4-Cl | — |
| 22(a) | —(CH₂)₃—(4-morpholinyl) | H | H | — |
| 22(b) | —(CH₂)₃—(1-piperidinyl) | H | H | — |
| 22(c) | —(CH₂)₃—(1-pyrrolidinyl) | H | H | — |
| 22(d) | —(CH₂)₃—(4-methyl-1-piperazinyl) | H | H | — |
| 23(a) | —(CH₂)₃—N(CH₃)₂ | 4-CH₃ | H | — |
| 23(b) | —(CH₂)₃—N(CH₃)₂ | 5-CH₃ | H | — |
| 23(c) | —(CH₂)₃—N(CH₃)₂ | 6-CH₃ | H | — |
| 23(d) | —(CH₂)₃—N(CH₃)₂ | 5,6-(CH₃)₂ | H | — |
| 23(e) | —(CH₂)₃—N(CH₃)₂ | 6-OCH₃ | H | — |
| 67(c) | —(CH₂)₃—N(CH₃)₂ | H | H | — |

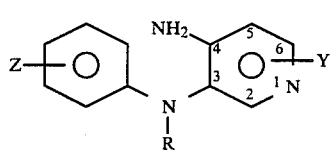

TABLE 2-continued

| Example No. | R | Y | Z | Salt |
|---|---|---|---|---|
| 18(f) | —(CH₂)₃—N(CH₃)₂ | H | H | — |
| 18(g) | —(CH₂)₃—N(CH₃)₂ | H | 4-CH₃ | — |
| 18(h) | —(CH₂)₃—N(CH₃)₂ | 6-OCH₃ | H | — |

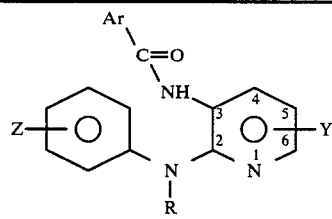

| 18(i) | —(CH₂)₃—N(CH₃)₂ | H | H | — |
| 23(f) | —(CH₂)₃—N(CH₃)₂ | 2-CH₃ | H | — |

| 18(j) | —(CH₂)₃—N(CH₃)₂ | H | H | — |

TABLE 3

| Example No. | R | Ar | Y | Z | Salt |
|---|---|---|---|---|---|
| 24 | —(CH₂)₃N(CH₃)₂ | C₆H₅— | H | H | fumarate |
| 25 | —(CH₂)₃N(CH₃)₂ | C₆H₅— | H | H | — |
| 26 (a) | —(CH₂)₃N(CH₃)₂ | C₆H₅— | H | 4-CH₃ | — |
| (b) | —(CH₂)₃N(CH₃)₂ | C₆H₅— | H | 2-OCH₃ | — |
| (c) | —(CH₂)₃N(CH₃)₂ | C₆H₅— | 5-OCH₃ | H | — |
| (d) | —(CH₂)₂N(CH₃)₂ | C₆H₅— | H | H | — |
| (e) | —(CH₂)₄N(CH₃)₂ | C₆H₅— | H | H | — |
| (k) | —(CH₂)₃N(CH₃)₂ | C₆H₅— | H | 4-Cl | — |
| (l) | —(CH₂)₃N(CH₃)₂ | C₆H₅— | H | 4-Br | — |
| 27 | —(CH₂)₃—(1-phthalimido) | C₆H₅— | H | H | — |
| 28 | —(CH₂)₃N(CH₃)₂ | 2-F—C₆H₄— | H | H | oxalate |
| 29 | —(CH₂)₃N(CH₃)₂ | 2-Cl—C₆H₄— | H | H | — |
| 30 | —(CH₂)₃N(CH₃)₂ | 2-Br—C₆H₄— | H | H | oxalate |
| 31 | —CH₃ | C₆H₅— | H | H | — |
| 32 | —CH₃ | 4-Cl—C₆H₄— | H | H | — |
| 33 (a) | —(CH₂)₃—(4-morpholinyl) | C₆H₅— | H | H | — |
| (b) | —(CH₂)₃—(1-piperidinyl) | C₆H₅— | H | H | — |
| (c) | —(CH₂)₃—(1-pyrrolidinyl) | C₆H₅— | H | H | — |
| (d) | —(CH₂)₃—(4-methyl-1-piperazinyl | C₆H₅— | H | H | — |
| 34 (a) | —(CH₂)₃N(CH₃)₂ | 2-thienyl | H | H | — |
| (b) | —(CH₂)₃N(CH₃)₂ | 3-thienyl | H | H | — |
| 35 | —(CH₂)₃N(CH₃)₂ | 2-pyridinyl | H | H | oxalate |
| 36 (a) | —(CH₂)₃N(CH₃)₂ | 3-pyridinyl | H | H | oxalate |
| (b) | —(CH₂)₃N(CH₃)₂ | 4-pyridinyl | H | H | oxalate |
| 37 (a) | —(CH₂)₃N(CH₃)₂ | C₆H₅ | 4-CH₃— | H | — |
| (b) | —(CH₂)₃N(CH₃)₂ | C₆H₅— | 5-CH₃— | H | — |
| (c) | —(CH₂)₃N(CH₃)₂ | C₆H₅— | 6-CH₃— | H | — |
| (d) | —(CH₂)₃N(CH₃)₂ | C₆H₅— | 5,6-(CH₃)₂ | H | — |
| (e) | —(CH₂)₃N(CH₃)₂ | C₆H₅— | 6-OCH₃ | H | — |
| 38 | —(CH₂)₃N(CH₃)₂ | 2-NO₂C₆H₄— | H | H | — |
| 39 | —CH₃ | 2-Br—C₆H₄— | H | 4-Cl | — |
| 40 | —CH₃ | 2-Cl—C₆H₄— | H | 4-Cl | — |
| 41 | —CH₃ | 2-F—C₆H₄— | H | 4-Cl | — |
| 42 | —CH₃ | 2-NO₂—C₆H₄— | H | 4-Cl | — |
| 43 | —CH₃ | 2-Br—C₆H₄— | H | H | — |
| 44 | —CH₃ | 2-Cl—C₆H₄— | H | H | — |

TABLE 3-continued

| Example No. | R | Ar | Y | Z | Salt |
|---|---|---|---|---|---|
| 45 | —CH₃ | 2-F—C₆H₄— | H | H | — |
| 46 | —CH₃ | 2-pyrido | H | 4-Cl | — |
| 67 (d) | —(CH₂)₃N(CH₃)₂ | C₆H₅— | H | H | — |

[Structure: Ar-C(=O)-NH attached to pyridine ring (positions 2,3,4,5,6 with N) linked via N-R to Z-phenyl]

| | | | | | |
|---|---|---|---|---|---|
| 26 (f) | —(CH₂)₃N(CH₃)₂ | C₆H₅— | H | H | — |
| (g) | —(CH₂)₃N(CH₃)₂ | C₆H₅— | H | 4-CH₃ | — |
| (h) | —(CH₂)₃N(CH₃)₂ | C₆H₅— | 6-OCH₃ | H | — |

[Structure: Ar-C(=O)-NH attached to pyridine ring (positions 2,3,4,5,6 with N at 1) linked via N-R to Z-phenyl]

| | | | | | |
|---|---|---|---|---|---|
| 26 (i) | —(CH₂)₃N(CH₃)₂ | C₆H₅— | H | H | — |
| 37 (f) | —(CH₂)₃N(CH₃)₂ | C₆H₅— | 2-CH₃ | H | — |

[Structure: Ar-C(=O)-NH attached to pyrazine ring linked via N-R to Z-phenyl]

| | | | | | |
|---|---|---|---|---|---|
| 26 (j) | —(CH₂)₃N(CH₃)₂ | C₆H₅— | H | H | — |

TABLE 4

| Example No. | alk¹-Q | Ar | Y | Z | Salt |
|---|---|---|---|---|---|

[Structure: tricyclic with phenyl ring (positions 7,8,9,10), central ring with N at 11 and alk¹-Q substituent, and pyridine ring (positions 1-5) with Y; Ar-C= at position 6, N at 5; Z on phenyl]

| Example No. | alk¹-Q | Ar | Y | Z | Salt |
|---|---|---|---|---|---|
| 47 | —(CH₂)₃N(CH₃)₂ | C₆H₅— | H | H | fumarate |
| 48 (a) | —(CH₂)₂N(CH₃)₂ | C₆H₅— | H | H | fumarate |
| (b) | —(CH₂)₄N(CH₃)₂ | C₆H₅— | H | H | fumarate |
| 49 | —(CH₂)₃N(CH₃)₂ | 2-F—C₆H₄— | H | H | — |
| 50 | —(CH₂)₃N(CH₃)₂ | 2-Cl—C₆H₄— | H | H | — |
| 51 | —(CH₂)₃N(CH₃)₂ | 2-Br—C₆H₄— | H | H | — |
| 52 | —(CH₂)₃N(CH₃)₂ | 2-NO₂—C₆H₄— | H | H | HCl |
| 53 (a) | —(CH₂)₃N(CH₃)₂ | C₆H₅— | H | 8-CH₃ | fumarate |
| (b) | —(CH₂)₃N(CH₃)₂ | C₆H₅— | H | 9-OCH₃ | fumarate |
| (c) | —(CH₂)₃N(CH₃)₂ | 4-Cl—C₆H₄— | H | H | fumarate |
| (i) | —(CH₂)₃—(1-phthalimido | C₆H₅— | H | H | — |
| (j) | —(CH₂)₃—N(CH₃)[C(O)OCH₃] | C₆H₅— | H | H | — |
| (k) | —(CH₂)₃N(CH₃)₂ | C₆H₅— | H | 8-Cl | fumarate |
| (l) | —(CH₂)₃N(CH₃)₂ | C₆H₅— | H | 8-Br | fumarate |
| 54 (a) | —(CH₂)₃—(4-morpholinyl) | C₆H₅— | H | H | — |
| (b) | —(CH₂)₃—(1-piperidinyl) | C₆H₅— | H | H | — |
| (c) | —(CH₂)₃—(1-pyrrolidinyl) | C₆H₅— | H | H | — |
| (d) | —(CH₂)₃—(4-methyl-1- | C₆H₅— | H | H | — |

TABLE 4-continued

| Example No. | alk¹-Q | Ar | Y | Z | Salt |
|---|---|---|---|---|---|
| | piperazinyl) | | | | |
| 55 (a) | —(CH₂)₃N(CH₃)₂ | 2-thienyl | H | H | — |
| (b) | —(CH₂)₃N(CH₃)₂ | 3-thienyl | H | H | — |
| 56 (a) | —(CH₂)₃N(CH₃)₂ | 2-pyridinyl | H | H | — |
| (b) | —(CH₂)₃N(CH₃)₂ | 3-pyridinyl | H | H | — |
| (c) | —(CH₂)₃N(CH₃)₂ | 4-pyridinyl | H | H | — |
| 57 (a) | —(CH₂)₃N(CH₃)₂ | C₆H₅— | 4-CH₃ | H | fumarate |
| (b) | —(CH₂)₃N(CH₃)₂ | C₆H₅— | 3-CH₃ | H | fumarate |
| (c) | —(CH₂)₃N(CH₃)₂ | C₆H₅— | 2-CH₃ | H | fumarate |
| (d) | —(CH₂)₃N(CH₃)₂ | C₆H₅— | 2,3-(CH₃)₂ | H | fumarate |
| (e) | —(CH₂)₃N(CH₃)₂ | C₆H₅— | 2-OCH₃ | H | fumarate |
| 58 | —CH₃ | 2Cl—C₆H₄ | H | 8-Cl | — |
| 59 | —CH₃ | 2-F—C₆H₄— | H | 8-Cl | — |
| 60 | —CH₃ | 2-Br—C₆H₄— | H | 8-Cl | — |
| 61 | —CH₃ | 2-NO₂—C₆H₄— | H | 8-Cl | — |
| 62 | —CH₃ | 2-Cl—C₆H₄— | H | H | — |
| 63 | —CH₃ | 2-Br—C₆H₄— | H | H | — |
| 64 | —CH₃ | 2-F—C₆H₄— | H | H | — |
| 65 | —CH₃ | C₆H₅— | H | H | — |
| 66 | —CH₃ | C₆H₅— | H | 8-Cl | — |
| 67 (e) | —(CH₂)₃N(CH₃)₂ | C₆H₅— | H | H | fumarate |

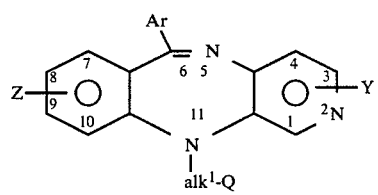

| 53 (d) | —(CH₂)₃N(CH₃)₂ | C₆H₅— | H | H | — |
|---|---|---|---|---|---|
| (e) | —(CH₂)₃N(CH₃)₂ | C₆H₅— | H | 8-CH₃ | — |
| (f) | —(CH₂)₃N(CH₃)₂ | C₆H₅— | 3-OCH₃ | H | — |

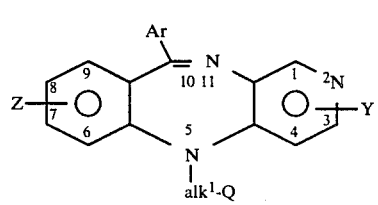

| (g) | —(CH₂)₃N(CH₃)₂ | C₆H₅— | H | H | fumarate |
|---|---|---|---|---|---|
| 57 (f) | —(CH₂)₃N(CH₃)₂ | C₆H₅— | 1-CH₃ | H | fumarate |

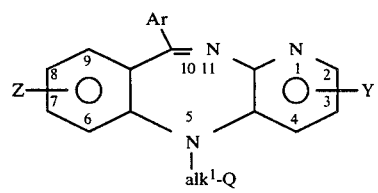

| 53 (h) | —(CH₂)₃N(CH₃)₂ | C₆H₅— | H | H | fumarate |
|---|---|---|---|---|---|

FORMULATION AND ADMINISTRATION

Effective quantities of the foregoing pharmacologically active compounds of Formula X may be administered to humans for therapeutic purposes according to usual modes of administration and in usual forms, such as orally in solutions, emulsions, suspensions, pills, tablets and capsules, in pharmaceutically acceptable carriers and parenterally in the form of sterile solutions.

Exemplary of solid carriers for oral administration are such as lactose, magnesium, stearate, terra alba, sucrose, talc, stearic acid, gelatin, agar, pectin or acacia.

Exemplary of liquid carriers for oral administration are vegetable oils and water.

For intramuscular administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 10, 25, 50, or 100 milligrams or even higher, preferably administered three or four times per day, depending, of course, upon the emergency of the situation, the compound used, and the particular result desired. Twenty-five to 200 milligrams appears optimum per unit dose or usual broader ranges appear to be about 10 to 500 milligrams per unit dose. Daily dosages usually required should range from about 0.3 to about 20 mg/kg/day, preferably 0.3 to 10 mg/kg for the more active compounds. The active ingredients of the invention may be combined with other compatible pharmacologically active agents. It is only necessary that the active ingredient constitute an effective amount; i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician.

The following formulations are representative for the pharmacologically active compounds of this invention.

FORMULATIONS

1. Capsules

Capsules of 10 mg and 50 mg of active ingredient per capsule are prepared. With the higher amounts of active ingredient, reduction may be made in the amount of lactose.

| Typical blend for encapsulation | 10 mg. Per Capsule | 50 mg. Per Capsule |
|---|---|---|
| Active ingredient, as salt | 10 | 50 |
| Lactose | 259 | 219 |
| Starch | 126 | 126 |
| Magnesium stearate | 4 | 4 |
| Total | 399 | 399 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

2. Tablets

A typical formulation for a tablet containing 5.0 mg of active ingredient per tablet follows. The formulation may be used for other strengths of active ingredient by adjustment of weight of dicalcium phosphate.

| | Per Tablet, mg. |
|---|---|
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

3. Injectable—2% sterile solution

| | Per cc |
|---|---|
| Active ingredient mg | 20 |
| Preservative, e.g., chlorobutanol, w/vol. percent | 0.5 |
| Water for injection q.s. | |

Prepare solution, clarify by filtration, fill into vials, seal and autoclave.

Various modifications and equivalents will be apparent to one skilled in the art and may be made in the compounds, compositions and methods of the present invention without departing from the spirit and scope thereof, and it is therefore understood that the invention is to be limited only by the scope of the appended claims.

What is claimed is:

1. A compound selected from the group having the formula:

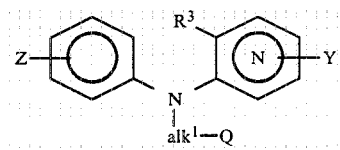

wherein;
Q is selected from the group consisting of hydrogen, $-NR^1R^2$ or halogen;
$R^1$ and $R^2$ are loweralkyl;
$R^3$ is selected from the group consisting of nitro, amino or aroylamino (ArCONH—);
Ar is selected from the group consisting of 2 or 3-thienyl, 2, 3 or 4 pyridinyl, phenyl or phenyl substituted by 1 to 3 radicals selected from halo, loweralkyl, loweralkoxy, trifluoromethyl, or nitro and may be the same or different;
$alk^1$ is a straight or branched hydrocarbon chain containing 1–8 carbon atoms;
Z is selected from the group consisting of hydrogen, halogen, loweralkyl, loweralkoxy or nitro;
Y is selected from the group consisting of hydrogen or 1–2 radicals selected from loweralkyl or loweralkoxy and may be the same or different;
and the acid addition salts thereof.

2. A compound of claim 1 wherein $R^3$ is a nitro group.

3. A compound of claim 1 wherein $R^3$ is an amino group.

4. A compound of claim 1 wherein $R^3$ is an aroylamino group.

5. A compound of claim 1 which is N-methyl-3-nitro-N-phenyl-2-pyridinamine.

6. A compound of claim 1 which is N-methyl-3-nitro-N-phenyl-2-pyridinamine hydrochloride.

7. A compound of claim 1 which is N-(4-chlorophenyl)-N-methyl-3-nitro-2-pyridinamine.

8. A compound of claim 1 which is N,N-dimethyl-N'-(3-nitro-2-pyridinyl)-N'-phenylpropanediamine.

9. A compound of claim 1 which is N,N-dimethyl-N'-(3-nitro-2-pyridinyl)-N'-phenylpropanediamine fumarate.

10. A compound of claim 1 which is $N^2$-[3-dimethylamino)propyl]-$N^2$-phenyl-2,3-pyridinediamine.

11. A compound of claim 1 which is $N^2$-[3-dimethylamino)propyl]-$N^2$-phenyl-2,3-pyridinediamine dihydrochloride.

12. A compound of claim 1 which is $N^2$-methyl-$N^2$-phenyl-2,3-pyridinediamine.

13. A compound of claim 1 which is $N^2$-methyl-$N^2$-phenyl-2,3-pyridinediamine monohydrochloride.

14. A compound of claim 1 which is $N^2$-(4-chlorophenyl)-$N^2$-methyl-2,3-pyridinediamine.

15. A compound of claim 1 which is N-[2-[[3-(dimethylamino)propyl]phenylamino]-3-pyridinyl]benzamide fumarate[1:1.5].

16. A compound of claim 1 which is N-[2-[[3-(dimethylamino)propyl]phenylamino]-3-pyridinyl]benzamide.

17. A compound of claim 1 which is N-[2-[[3-(dimethylamino)propyl]phenylamino]-3-pyridinyl]-2-fluorobenzamide.

18. A compound of claim 1 which is N-[2-[[3-(dimethylamino)propyl]phenylamino]-3-pyridinyl]-2-fluorobenzamide oxalate[1:1].

19. A compound of claim 1 which is 2-chloro-N-[2-[[3-(dimethylamino)propyl]phenylamino]-3-pyridinyl]benzamide.

20. A compound of claim 1 which is 2-bromo-N-[2-[[3-(dimethylamino)propyl]phenylamino]-3-pyridinyl]benzamide.

21. A compound of claim 1 which is 2-bromo-N-[2-[[3-(dimethylamino)propyl]phenylamino]-3-pyridinyl]benzamide oxalate[1:1].

22. A compound of claim 1 which is 2-bromo-N-[2-[[3-(dimethylamino)propyl]phenylamino]-3-pyridinyl]benzamide fumarate.

23. A compound of claim 1 which is N-[2-[[3-(dimethylamino)propyl]phenylamino]-3-pyridinyl]-2-pyridinecarboxamide.

24. A compound of claim 1 which is N-[2-[[3-(dimethylamino)propyl]phenylamino]-3-pyridinyl]-2-pyridinecarboxamide oxalate.

25. A compound of claim 1 which is N-[2-[[3-(dimethylamino)propyl]phenylamino]-3-pyridinyl]-2-nitrobenzamide.

26. A compound of claim 1 which is 2-bromo-N-[2-[4-chlorophenyl)methylamino]-3-pyridinyl]benzamide.

27. A compound of claim 1 which is 2-chloro-N-[2-[(4-chlorophenyl)methylamino]-3-pyridinyl]benzamide.

28. A compound of claim 1 which is N-[2-[(4-chlorophenyl)methylamino]-3-pyridinyl]-2-fluorobenzamide.

29. A compound of claim 1 which is N-[2-[(4-chlorophenyl)methylamino]-3-pyridinyl]-2-nitrobenzamide.

30. A compound of claim 1 which is 2-bromo-N-[2-(methylphenylamino)-3-pyridinyl]benzamide.

31. A compound of claim 1 which is 2-chloro-N-[2-(methylphenylamino)-3-pyridinyl]benzamide.

32. A compound of claim 1 which is 2-fluoro-N-[2-(methylphenylamino)-3-pyridinyl]benzamide.

* * * * *